United States Patent
Tidmarsh et al.

(10) Patent No.: US 10,406,201 B2
(45) Date of Patent: Sep. 10, 2019

(54) METHODS FOR ADMINISTERING ANGIOTENSIN II

(71) Applicant: La Jolla Pharma, LLC, San Diego, CA (US)

(72) Inventors: George Tidmarsh, Portola Valley, CA (US); Lakhmir Chawla, San Diego, CA (US)

(73) Assignee: La Jolla Pharma, LLC, San Diego, CA (US)

( * ) Notice: Subject to any disclaimer, the term of this patent is extended or adjusted under 35 U.S.C. 154(b) by 0 days.

(21) Appl. No.: 15/400,275

(22) Filed: Jan. 6, 2017

(65) Prior Publication Data

US 2017/0224761 A1    Aug. 10, 2017

Related U.S. Application Data

(60) Provisional application No. 62/347,292, filed on Jun. 8, 2016, provisional application No. 62/276,171, filed on Jan. 7, 2016.

(51) Int. Cl.
| | |
|---|---|
| *A61K 38/08* | (2019.01) |
| *C12Q 1/00* | (2006.01) |
| *G01N 33/74* | (2006.01) |
| *A61K 9/00* | (2006.01) |

(52) U.S. Cl.
CPC .......... *A61K 38/085* (2013.01); *A61K 9/0019* (2013.01); *C12Q 1/00* (2013.01); *G01N 33/74* (2013.01); *G01N 2410/02* (2013.01); *G01N 2800/32* (2013.01); *G01N 2800/52* (2013.01)

(58) Field of Classification Search
CPC ................ A61K 38/085; A61K 38/556; A61K 39/3955; C07K 7/06; C07K 14/4702
See application file for complete search history.

(56) References Cited

U.S. PATENT DOCUMENTS

| | | | |
|---|---|---|---|
| 4,330,532 A | 5/1982 | Nyeki et al. | |
| 5,216,025 A | 6/1993 | Gross et al. | |
| 5,444,067 A | 8/1995 | Kivlighn et al. | |
| 6,592,865 B2 | 7/2003 | Parry et al. | |
| 7,666,408 B2 | 2/2010 | Bachmann | |
| 9,220,745 B2 | 12/2015 | Chawla | |
| 9,457,059 B2 | 10/2016 | Tidmarsh | |
| 9,572,856 B2 | 2/2017 | Chawla | |
| 9,867,863 B2 | 1/2018 | Chawla | |
| 10,028,995 B2 | 7/2018 | Chawla | |
| 2010/0172862 A1 | 7/2010 | Correia et al. | |
| 2011/0144026 A1 | 6/2011 | Chawla | |
| 2016/0074465 A1 | 3/2016 | Tidmarsh | |
| 2016/0129072 A1 | 5/2016 | Chawla | |
| 2017/0014471 A1 | 1/2017 | Tidmarsh | |
| 2017/0095526 A1 | 4/2017 | Chawla | |
| 2017/0196931 A1 | 7/2017 | Chawla | |
| 2018/0133282 A1 | 5/2018 | Chawla | |
| 2018/0311306 A1 | 11/2018 | Tidmarsh et al. | |

FOREIGN PATENT DOCUMENTS

| | | |
|---|---|---|
| WO | WO-2014/176534 A1 | 10/2014 |
| WO | WO-2015/095535 A1 | 6/2015 |
| WO | WO-2016/007589 A1 | 1/2016 |
| WO | WO-2017/120438 A1 | 7/2017 |
| WO | WO-2017/120440 A1 | 7/2017 |
| WO | WO-2018/191678 A1 | 10/2018 |

OTHER PUBLICATIONS

Leone et al., Critical Care, 2015, 19:101. (Year: 2015).*
Ferreira et al., JAMA, Oct. 10, 2001, vol. 286, No. 14. (Year: 2001).*
Zambelli et al., Intensive Care Medicine Experimental, 2015, 3:8, 1-17. (Year: 2015).*
Al-Merani et al., "The Half-Lives of Angiotensin II, Angiotensin II-Amide, Angiotensin III, SAR1-ALA9-Angiotensin II and Renin in the Circulatory System of the Rat," J Physiol, 278: 471-490 (1978).
Ames, R.P., et al., "Prolonged Infusions of Angiotensin Ii and Norepinephrine and Blood Pressure,Electrolyte Balance, and Aldosterone and Cortisol Secretion in Normal Man and in Cirrhosis with Ascites," J Clin Invest, 44:1171-86 (1965).
Angus et al., Epidemiology of severe sepsis in the United States: Analysis of incidence, outcome, and associated costs of care. Crit Care Med 29:1303-1310 (2001).
Asfar et al., "Angiotensin-II: more than just another vasoconstrictor to treat septic shock-induced hypotension?" Crit Care Med, 42(8): 1961-1963 (2014).
Avazini et al., "High pulse pressure and low mean arterial pressure: two predictors of death after a myocardial infarction," J Hypertens, 24 (12): 2377-2385 (2006).
Bachem (downloaded on Mar. 31, 2017 from URL: <http://shop.bachem.com/h-1705.html>).
Bachem (downloaded online on Dec. 15, 2014 from URL: <http://shop.bachem.com/h-1705-1.html>).
Bachem2010 (downloaded on Sep. 22, 2015) from URL:<http://www.archive.org/web/20100730002830/http://shop.bachem.com/ep6sf/peptides-and-biochemicals/angiotensins-and-related-peptides/c4750-c4771-p2.html?sorter=sortNumber-asc>.
Bagshaw et al., A Multi-Centre Evaluation of the Rifle Criteria for Early Acute Kidney Injury in Critically Ill Patients. Nephrol Dial Transplant Oct. 25 (Epub): (2007).
Basso et al., "History about the discovery of the renin-angiotensin system.," *Hypertension*, 38(6):1246-1249 (2001).
Bradley et al., "The Hemodynamic Effects of Angiotonin in Normal Man," J Clin Invest, 20(6): 715-719 (1941).
Busse, et al., "Angiotensin II may be useful for the treatment of hypotension in distributive shock, but a safe and efficacious dose is unknown," Crit Care, 18(Suppl 1): 160 (2014).

(Continued)

*Primary Examiner* — Kaipeen E Yang
(74) *Attorney, Agent, or Firm* — Foley Hoag LLP; David P. Halstead, J.D.; Allison Gilder

(57) ABSTRACT

The present disclosure relates to the use of angiotensin II, angiotensin III, or angiotensin IV in therapeutic methods for the treatment of hypotension, especially catecholamine-resistant hypotension.

16 Claims, No Drawings
Specification includes a Sequence Listing.

(56) References Cited

OTHER PUBLICATIONS

Campbell, D.J. "Do intravenous and subcutaneous angiotensin II increase blood pressure by different mechanisms?" Clin. Exper. Pharmacol. Physiol., 40:560-570 (2013).
Chemmwatch (downloaded online on Mar. 5, 2015 from URL: <http://www.chemwatch.net/product/angiotensin-ii-5-l-isoleucine-acetate-salt>.
Clinical Trial No. NCT01393782, "Intravenous AII for the Treatment of Severe Hypotension in High Output Shock: A Pilot Study," retrieved from the internet: https://clinicaltrials.gov/archive/NCT01393782/2013_03_14, on Nov. 30, 2016.
Daskalopoulos, G., et al., "Effects of captopril on renal function in patients with cirrhosis and ascites," J Hepatol, 4(3): 330-6 (1987).
del Greco, et al., "Clinical Experience with Angiotensin II in the Treatment of Shock," JAMA, 178(10): 130-135 (1961).
Dellinger, et al., "Surviving Sepsis Campaign Guidelines Committee including the Pediatric Subgroup: Surviving sepsis campaign: International guidelines for management of severe sepsis and septic shock: 2012," Crit Care Med, 41: 580-637 (2013).
Depasquale et al., "Effect of angiotensin II on the intace forearm veins of man," Circ Res, 13:239-245 (1963).
Downing, et al., "Effects of Angiotensin II and Norepinephrine on Ventricular Performance During Oligemic Shock," Yale J Biol Med, 36(6): 407-420 (1964).
Dworkin, M.J., et al.; "Nitric Oxide Inhibition Sustains Vasopressin-Induced Vasoconstriction," British Journal of Cancer; 71; 942-944 (1995).
Eadington et al., "Urinary dopamine response to angiotensin II is not abnormal in type 1 (insulin-dependent) diabetes mellitus," Nephrol Dial Transplant, 8(1):36-40 (1993).
Elias, N., "Norepinephrine," New World Encyclopedia, available online at http://www.newworldencyclopedia.org/entry/Norepinephrine, 5 pages, accessed on Sep. 2, 2016.
Eriksson et al., "Just the beginning: novel functions for angiotensin-converting enzymes," Curr Biol, 12(21): R745-R752 (2002).
Extended European Search Report issued by the European Patent Office in corresponding EP Application No. 15775357, dated Apr. 22, 2016.
Finnerty et al., "Evaluation of the pressor, cardiac, and renal hemodynamic properties of angiotensin II in man," Circ Res, 9:256-263 (1961).
Ginès, Pere, et al., "Hepatorenal syndrome," The Lancet, 362: 1819-27 (2003).
Goldsmith et al., Effect of a pressor infusion of angiotensin II on sympathetic activity and heartrate in normal humans. Circ Res 1991, 68(1 ):263-268.
Goldsmith et al., "Angiotensin II and Sympathetic Activity in Patients With Congestive Heart Failure," JACC, 15(5): 1107-1113 (1993).
Harrison-Bernard, et al., "The renal renin-angiotensin system," Adv Physiol Educ, 33(4): 270-4 (2009).
Helmy, A., et al., "Nitric oxide mediates the reduced vasoconstrictor response to angiotensin II in patients with preascitic cirrhosis," J Hepatol, 38(1): p. 44-50 (2003).
Heringlake et al., Renal Dysfuction according to the ADQI-RIFLE system and clinical practice patterns after cardiac surgery in Germany. Minerva Anestesiol 72:645-654 (2006).
Hou et al., "Ferulic acid inhibits vascular smooth muscle cell proliferation induced by angiotensin II," Eur J Pharmacol, 499(1-2): 85-90 (2004).
Hou et al., "Angiotensin II-induced Cardiac Fibrosis in the Rat Is Increased by Chronic Inhibition of Nitric Oxide Synthase," J Clin Invest, 96: 2469-2477 (1995).
International Search Report and Written Opinion for International Application No. PCT/US2017/012485 dated Apr. 27, 2017.
International Search Report and Written Opinion for International Application No. PCT/US2017/012487 dated Apr. 27, 2017.
International Search Report and Written Opinion for PCT/US2014/035511, dated Jul. 1, 2014.
Jackson et al., Enalapril overdose treated with anQiotensin infusion. Lancet 1993, 341 (8846):703.
Johnston, et al., "Outcomes of military patients treated at the UK Royal Centre for Deference Medicine 2007 to 2013," Critical Care, 18 (Supp 1): S57 (2014).
Jones, et al., "The Sequential Organ Failure Assessment score for predicting outcome in patients with severe sepsis and evidence of hypoperfusion at the time of emergency department presentation," Crit. Care Med., 37: 1649-1654 (2009).
Kakavas, S. et al. "Vasoactive Support in the Optimization of Post-Cardiac Arrest Hemodynamic Status: From Pharmacology to Clinical Practice," European Journal of Pharmacology 667 (2011) 32-40.
Kanaide et al., "Cellular Mechanism of Vasoconstriction Induced by Angiotensin II It Remains to be Determined," Circ Res, 93: 1015-1017 (2003).
Kanaparthi et al., "Distributive Shock," Medscape Reference, (Feb. 2013).
Kuitunen et al., Acute renal failure after cardiac surgery: evaluation of the RIFLE classification.Ann Thorac Surg 81:542-546, 2006.
Kürer et al., "Hepatorenal Syndrome," Der Anaesthesist; Zeitschrift Für Anästhesie, Intensivmedizin, Notfallund Katastrophenmedizin, Schmerzmedizin, Springer, Berlin, De, 55(1): 95-109 (Jan. 1, 2006).
LaGrange et al., "Effect of Intravenous Angiotensin II Infusion on Responses to Hypothalamic PVN Injection of Bicuculline," Hypertension, 42:1124-1129 (2003).
Laragh, J.H., et al., "Angiotensin II, Norepinephrine, and Renal Transport of Electrolytes and Water in Normal Man and in Cirrhosis with Ascites," J Clin Invest, 42(7): 1179-92 (1963).
Lata, et al., "Hepatorenal Syndrome," World J Gastroenterol, 18(36): 4978-4984 (2012).
Le et al., "Angiotensin IV is a potent agonist for constitutive active human AT1 receptors distinct roles of the n-and c-terminal residues of angiotensin II during AT1 receptor activation," J Biol Chem, 277(26): 23107-23110 (2002).
Lee et al., "34-year-old woman with hypotension, respiratory failure, fever, and an abdominal mass," Wes J Med, 158(5), 499 (1993).
Li, et al., "Changes in Sensitivity of Vascular Smooth Muscle to Calcium and Its Role in the Biphasic Change in Vascular Reactivity Following Hemorrhagic Shock in Rats," Chinese Critical Care Medicine, 17(11): 647-650 (2005).
Li, et al., "Changes in Sensitivity of Vascular Smooth Muscle to Calcium and Its Role in the Biphasic Change in Vascular Reactivity Following Hemorrhagic Shock in Rats," Chinese Critical Care Medicine, 17(11): 647-650 (2005). Abstract.
Lianos, E.A., et al., "Angiotensin-induced sodium excretion patterns in cirrhosis: role of renal prostaglandins," Kidney Int, 21(1): 70-7 (1982).
Lopes et al., Prognostic utility of RIFLE for acute renal failure in patients with sepsis. Crit Care 11 :408, 2007.
Lottermoser et al., "Differential Effect of Acute Angiotensin II Type 1 Receptor Blockade on the Vascular and Adrenal Response to Exogenous Angiotensin II in Humans," American Journal of Hypertension, 16: 445-452 (2003).
Mayo Clinic, Sepsis Symptoms—Mayo Clinic, Accessed on Jun. 12, 2015, Available Online at: http://www.mayoclinic.org/diseases-conditions/sepsis/basics/symptoms/con-con-20031900.
McCloy, R.M., et al., "Angiotensin-induced natriuresis in cirrhosis in the absence of endogenous aldosterone secretion," Ann Intern Med, 64(6): 1271-6 (1966).
Medscape (downloaded online on Jan. 2, 2015 from URL: <http://emedicine.medscape.com/article/907429-workup>).
Millar et al., "Activity of the renin-angiotensin system in acute severe asthma and the effect of angiotensin II on lung function," Thorax, 49(5):492-495 (1994).
Millar et al., "Angiotensin II potentiates methacholine-induced bronchoconstriction in human airway both in vitro and in vivo," The European Respiratory Journal, 8(11):1838-1841 (1995).
Morelli et al., Singer M: Effect of heart rate control with esmolol on hemodynamic and clinical outcomes in patients with septic shock: a randomized clinical trial. JAMA 2013, 31 0(16):1683-1691.
Morrell et al., "The Management of Severe Sepsis and Septic Shock," Infect Dis Clin N Am, 23(1): 485-501 (2009).

(56) References Cited

OTHER PUBLICATIONS

Myburgh et al., CAT Study investigators: A comparison of epinephrine and norepinephrine in critically ill patients. *Intensive Care Med* 2008, 34(12):2226-2234.
Nagamitsu et al., "Elevating blood pressure as a strategy to increase tumor-targeted delivery of macromolecular drug SMANCS: cases of advanced solid tumors," Jpn J Clin Oncol, 39(11):756-766 (2009).
Nassif, et al., "Angiotensin II in Treatment of Hypotensive States," JAMA, 183(9): 751-754 (1963).
National Health Services UK, "Low blood pressure (hypotension)—information prescription," available online at http://www.nhs.uk/conditions/blood-pressure-(low)/pages/introduction.aspx, 11 pages. (May 9, 2016).
Newby, D.E., et al., "Peripheral vascular tone in patients with cirrhosis: role of the renin-angiotensin and sympathetic nervous systems," Cardiovasc Res, 38(1): 221-8 (1998).
Newby, et al., "Enalapril overdose and the corrective effect of intravenous angiotensin II," Brit J Clin Pharmaco, 40(1): 103-104 (1995).
Niu, et al., "Lymphatic Hyporeactivity and Calcium Desensitization Following Hemorrhagic Shock," Shock, 37(4): 415-423 (2012).
O'Brien et al., "Terlipressin for norepinephrine-resistant septic shock," Lancet, 359(9313): 1209-1210 (2002).
Onohara et al., "Intra-arterial cis-platinum infusion with sodium thiosulfate protection and angiotensin II induced hypertension for treatment of hepatocellular carcinoma," Acta Radiol, 29(2):197-202 (1988).
Page, et al., "Angiotensin," Physiol Rev, 41: 331-390 (1961).
Pariente et al., "Acute Effects of Captopril on Systemic and Renal Hemodynamics and on Renal Function in Cirrhotic Patients with Ascites," Gastroenterology, 88(5): 1255-1259 (May 1, 1985).
Pickering, et al., "Recommendations for blood pressure measurement in humans and experimental animals: part 1: blood pressure measurement in humans: a statement for professionals from the Subcommittee of Professional and Public Education of the American Heart Association Council on High Blood Pressure Research," Circulation, 111: 697-716 (2005).
Rona G: Catecholamine cardiotoxicity. J Mol Cell Cardio/1985, 17(4 ):291-306.
Rose, et al., "Comprison of Effects of Angiotensin and Norepinephrine on Pulmonary Circulation, Systemic Arteries and Veins, and Systemic Vascular Capacity in the Dog," Circulation, 25(1): 247-252 (1962).
Ryding, J. et al., "Reversal of 'Refractory Septic Shock' vby Infusion of Amrinone and Angiotensin II in an Anthracycline-Treated Patient," Chest, 107, 201-203 (1995).
Saino et al., "Intracoronary angiotensin II potentiates coronary sympathetic vasoconstriction in humans," Circulation 96(1):148-153 (1997).
Salerno, Francesco, et al., "Diagnosis, Prevention and Treatment of Hepatorenal Syndrome in Cirrhosis," Gut Journal, 56: 1310-1318 (2007).
Sansoe, G., et al., "Inappropriately low angiotensin II generation: a factor determining reduced kidney function and survival in patients with decompensated cirrhosis," J Hepatol, 40(3): 417-23 (2004).
Schroeder, E.T., et al. "Renal Failure in Patients with Cirrhosis of the Liver* III. Evaluation of Intrarenal Blood Flow by Para-aminohippurate Extraction and Response to Angiotensin," American Journal of of Medicine; 43: 887-896 (1967).
Simon et al., "Duration and magnitude of hypotension and monocyte deactivation in patients with community-acquired pneumonia," Shock, 36(6): 553-559 (2012).
Struthers et al., Review of aldosterone- and angiotensin II-induced target organ damage and prevention. Cardiovasc Res 2004, 61 (4 ):663-670.
Thomas, et al., "Administration of angiotensin II in refractory septic shock," Crit Care Med, 19:1084-1086 (1991).

Tremblay et al., "Effect of hypotension preceding death on the function of lungs from donors with nonbeating hearts," J Heart Lung Transplant, 15(3): 260-268 (1996).
Trilli et al., Lisinopril overdose and management with intravenous angiotensin II. Ann Pharmacother 1994, 28(1 0): 1165-1168.
Uchino et al., "Acute Renal Failure in Critically Ill Patients: A Multinational, Multicenter Study," JAMA, 294: 813-818 (2005).
Unknown author (2005). NSC107678. [chemical structure] http://www.dspace.cam.ac.uk/handle/1810/88629.
Vaile, et al., "Angiotensin II modulates cardiovascular autonomic control in the absence of baroreflex loading," Heart, 80: 127-133 (1998).
Valdes et al., "Administration of Angiotensin II and a Bradykinin B2 Receptor Blocker in Midpregnancy Impairs Gestational Outcome in Guinea Pigs," Reproductive Biology and Endocrinology, 12(49): 1-8 (2014).
Vincent et al., "Prophylactic angiotensin II infusion during spinal anesthesia for elective cesarean delivery," Anesthesiology, 88(6):1475-1479 (1998).
Vincent et al., The SOFA (Sepsis-related Organ Failure Assessment) score to describe organ dysfunction/failure. On behalf of the Working Group on Sepsis-Related Problems of the European Society of Intensive Care Medicine. Intensive Care Med 1996, 22(7):707-71 0.
Vincent, et al., "Circulatory Shock," N Engl J Med, 369(18): 1726-1734 (2013).
Vittorio et al., "Vasopressor response to angiotensin II infusion in patients with chronic heart failure receiving beta-blockers," Circulation, 107(2):290-293 (2003).
Vos et al., "Efficacy of intrarenal ACE-inhibition estimated from the renal response to angiotensin I and II in humans," Kidney Int, 47(1):274-281 (1995).
Vos et al., "The origin of urinary angiotensins in humans," J Am Soc Nephrol, 5(2):215-223 (1994).
Wadei et al., "Hepatorenal Syndrome: Pathophysiology and Management," Clin J Am Soc Nephrol, 1: 1066-1079 (2006).
Walpole et al., "The weight of nations: an estimation of adult human biomass," BMC Public Health, 12: 439 (2012).
Wan, et al., "Angiotensin II in experimental hyperdynamic sepsis," Crit Care; 13: R190 (2009).
Weber, "Extracellular matrix remodeling in heart failure: a role for de novo angiotensin II generation," Circulation, 96(11):4065-4082 (1997).
Weisgerber et al., "Vasopressinanaloga als Ultima ratio bei einer schweren Intoxikation mit Vasodilatanzien," Dtsch med Wochenschr, 128(42): 2189-2192 (2003).
Whiteley, et al., "Treatment of Hypotension in Septic Shock," Lancet 1996, 347(9001)::622.
Wilson et al., U.S. trends in CABG hospital volume: the effect of adding cardiac surgery programs. Health Aff 26:162-168, 2007.
Wray et al., Severe septic shock unresponsive to noradrenaline. Lancet 1995, 346(8990): 1604.
Yunge et al., "Angiotensin for septic shock unresponsive to noradrenaline," Archives of Disease in Childhood, 82: 388-89, 2000.
Ziegler, T.W., "Hepatorenal Syndrome: A Disease Mediated by the Intrarenal Action of Renin," Medical Hypotheses, 2(1): 15-21 (1976).
Chawla et al., "Intravenous Angiotensin II for the Treatment of High-output Shock (ATHOS Trial): A Pilot Study," Crit Care,18(5): 534 (2014).
Cohn et al., "Studies in Clinical Shock and Hypotension. Ii. Hemodynamic Effects of Norepinephrine and Angiotensin," J Clin Invest, 44: 1494-1504 (1965).
Correa et al., "Angiotensin II in Septic Shock: Effects on Tissue Perfusion, Organ Function, and Mitochondrial Respiration in a Porcine Model of Fecal Peritonitis," Crit Care Med, 42(8):e550-e559 (2014).
Cziraki et al., "Quantification of Pulmonary Capillary Endothelium-bound Angiotensin Converting Enzyme Inhibition in Man," Gen Pharmacol, 35(4): 213-218 (2000).
Derrick et al., "Adjunctive Use of a Biologic Pressor Agent, Angiotensin, in Management of Shock," Circulation, 25: 263-267 (1962).

(56) References Cited

OTHER PUBLICATIONS

Kimmoun et al., "Angiotensin II: A New Approach for Refractory Shock Management?," Crit Care,18(6): 694 (2014).
Landry et al., "Vasopressin Pressor Hypersensitivity in Vasodilatory Septic Shock," Crit Care Med, 25(8): 1279-1282 (1997).
Orfanos et al., "Assay of Pulmonary Microvascular Endothelial Angiotensin-converting Enzyme In Vivo: Comparison of Three Probes," Toxicol Appl Pharmacol,124(1): 99-111 (1994).
Orfanos et al., "Pulmonary Capillary Endothelium-bound Angiotensin-converting Enzyme Activity in Acute Lung Injury," Circulation, 102(16): 2011-2018 (2000).
Orfanos et al., "Pulmonary Capillary Endothelium-bound Angiotensin-converting Enzyme Activity in Humans," Circulation, 99(12):1593-1599 (1999).
Russell et al., "Vasopressin Versus Norepinephrine Infusion in Patients with Septic Shock," N Engl J Med, 358(9): 877-887 (2008).
Ware et al., "The Acute Respiratory Distress Syndrome," N Engl J Med, 342(18):1334-1349 (2000).
"International Guidelines for Management of Severe Sepsis and Septic Shock," Society of Critical Care Medicine, European Society of Intensive Care Medicine, (2013).
Abuelo, "Normotensive Ischemic Acute Renal Failure," N Engl J Med, 357:797-805 (2007).
Chawla et al., "The Use of Angiotensin II in Distributive Shock," Critical Care, 20(1):137-1 (2016).
Collier et al., "Comparison of Effects of Locally Infused Angiotensin I and II on Hand Veins and Forearm Arteries in Man: Evidence for Converting Enzyme Activity in Limb Vessels," Clin Sci Mol Med, 47(2):189-192 (1974).
Egner et al., "Noninvasive Blood Pressure Monitoring: A Review," NAVC Clinician's Brief, 71-74 (2010).
Extended European Search Report for EP Application No. 18158219.8 dated Jun. 28, 2018.
Fyhrquist et al., "Renin-Angiotensin System Reviewed," Journal of Internal Medicine, 264: 224-236 (2008).
Griffin, "Angiotensin II Causes Vascular Hypertrophy in Part by a Non-pressor Mechanism," Hypertension, 17: 626-635 (1991).
International Search Report and Written Opinion for International Application No. PCT/US2018/027593 dated Jul. 22, 2018.
Khanna et al., "Angiotensin II for the Treatment of Vasodilatory Shock," The New England Journal of Medicine, 277: 419-430 (2017).
Kienbaum et al., "Alterations in Forearm Vascular Reactivity in Patients with Septic Shock," Anaesthesia, 63: 121-128 (2008).
Kopacova et al., "Hepatorenal syndrome," World Journal of Gastroenterology, 18(36):4978-4984 (2012).
Lankadeva, "Urinary Oxygenation as a Surrogate Measure of Medullary Oxygenation During Angiotensin II Therapy in Septic Acute Kidney Injury," Crit Care Med, 46(1): e41-e48 (2018).
Leibly et al., "Stabilizing additives added during cell lysis aid in the solubilization of recombinant proteins," PLoS One 7(12): e52482 (2012).
Medlej, "Mean Arterial Pressure (MAP)," MDCalc, pp. 1-2 available online: https://www.mdcalc.com/mean-arterial-pressure-map. (accessed on Dec. 20, 2017).
NCBI Database, PubChem Compound Database, PubChem CID: 172198.
NCBI Database, PubChem Compound Database, PubChem CID: 73354658.
Rahman, "Acute Kidney Injury: A Guide to Diagnosis and Management," Am Fam Physician, 86(7): 631-639 (2012).
Sigma-Aldrich Co., Production Information, Angiotensin II, human, Apr. 13, 2012.
Swartz et al., "Converting Enzyme Inhibition in Essential Hypertension: The Hypotensive Response does Not Reflect only Reduced Angiotensin II Formation," Hypertension, 1: 106-111 (1979).
Tumlin et al., "Outcomes in Patients with Vasodilatory Shock and Renal Replacement Therapy Treated with Intravenous Angiotensin II," Critical Care Medicine, 46(6):949-957 (2018).

Workeneh, "Acute Kidney Injury Treatment & Management," Medscape, https://emedicine.medscape.com/article/243492-treatment, Retrieved on May 14, 2018, 32 pages (Year: 2017).
Xue et al., "Sensitization of Slow Pressor Angiotensin II (Ang II)—Initiated Hypertension," Hypertension, 59(2): 459-466 (2012).
Boehm, "Angiotensin-Converting Enzyme 2—A New Cardiac Regulator," N Engl J Med, 347(22): 1795-1797 (2002).
Lehman et al., "Hypotension as a Risk Factor for Acute Kidney Injury in ICU Patients," Computing in Cardiology, 37:1095-1098 (2010).
Miller et al., "Impact of gender on the renal response to angiotensin II," Kidney International, 55:278-285 (1999).
"Angiotensin in septic kidney injury trial (ASK-IT)," https://clinicaltrials.gov/ct2/show/NCT00711789 (2008).
"Angiotensin in septic kidney injury trial," https://anzctr.org.au/Trial/Registration/TrialReview.aspx?id+2037&isClinicalTrial=True, (2008).
Ahmed et al., "The effect of angiotensin on myocardial contractility," J Clin Pharmacol, 15(4.1):276-285 (1975).
Bentsen et al., "Chronically impaired autoregulation of cerebral blood flow in long-term diabetics," Stroke, 6(5):497-502 (1975).
Bhimma et al., "Pediatric hepatorenal syndrome workup," Medscape Drugs, Disease & Procedures, (2011).
Bianco et al., "Angiotensin infusion effects on left ventricular function. Assessment in normal subjects and in patients with coronary disease," Chest, 77(2):172-175 (1980).
Brod et al., "Comparison of haemodynamic effects of equipressor doses of intravenous angiotensin of noradrenaline in man," Clinical Science, 36(2):161-172 (1969).
Brown et al., "The effects of intravenous angiotensin II upon blood pressure and sodium and urate excretion in human pregnancy," J Hypertens, 6(6):457-464 (1988).
Catanzaro et al., "Angiotensin-Infusion Test Correlation with Renin Activity in Peripheral Venous Blood," Arch Intern Med, 122(1):10-17 (1968).
Chobanin et al., "The seventh report of the joint national committee on prevention, detection, evaluation, and treatment of high blood pressure: The JNC 7 report," Journal of the American Medical Association, 289(19):2560-2572 (2003).
Clinical Trial No. NCT00711789 "Angiotensin in Septic Kidney Trial ASK-IT," retrieved from the Internet: https://clinicaltrials.gov/ct2/show/NCT00711789, on Jan. 5, 2019.
Cokkinos et al., "Constancy of pressure-rate product in pacing-induced angina pectoris," Br Heart J, 38(1):39-42 (1976).
Cook et al., "Maternal angiotensin sensitivity and fetal Doppler umbilical artery flow waveforms," Br J Obstet Gynaecol, 98(7):698-702 (1991).
Enevoldsen et al., "Autoregulation and CO2 responses of cerebral blood flow in patients with acute severe head injury," J Neurosurg, 48(5):689-703, (1978).
Fridman et al., "Influence of AT1 receptor blockade on blood pressure renal haemodynamics and hormonal responses to intravenous angiotensin II infusion in hypertensive patients," Blood Press, 11(4):244-252 (2002).
Frolich et al., "Urinary prostaglandins. Identification and origin," J Clin Invest, 55(4):763-770 (1975).
Fukuchi et al., "Diagnostic Value of Plasma Renin Activity and Plasma Angiotensin II in Renovascular Hypertension," Japanese Circulation Journal, 39(7):823-827 (1975).
Genest, "The value of angiotensin infusion test in the diagnosis of true renovascular hypertension," American Heart Journal, 76(4):443-444 (1968).
Gordon et al., "A new Australian kindred with the syndrome of hypertension and hyperkalaemia has dysregulation of artrial natriuretic factor," J Hypertens, 6(4):S323-S326 (1988).
Gordon et al., "A renin-secreting tumour sensitive to changes in central blood volume (presumably via sympathetics) but not to circulating angiotensin II," Clin Exp Pharmacol Physiol, 17(3):185-189 (1990).
Gordon et al., "Angiotensin-responsive aldosterone-producing adenoma masquerades as idiopathic hyperaldosteronism (IHA: Adrenal hyperplasia) or low-renin essential hypertension," J Hypertens Suppl, 5(5):S103-S106 (1987).

(56) References Cited

OTHER PUBLICATIONS

Henriksen et al., "The effect of induced arterial hypertension upon regional blood flow in subcutaneous tissue in patients with arterial insufficiency of the legs," Scand J Clin Lab Invest, 35(2):115-120 (1975).
Hogewind et al., "Bartter's syndrome: An autosomal recessive disorder? Study of four patients in one generation of the same pedigree and their relatives," Acta Med Scand, 109(6):463-467 (1981).
Jezek et al., "Haemodynamic reaction to exercise and increased afterload in the detection of right heart failure in pulmonary diseaes," Cor et Vasa, 22(4):272-280 (1980).
Katayama et al., "Dynamic determinants of left ventricular early diastolic filling in old myocardial infarction," Jpn Circ J, 56(7):750-758 (1992).
Kaulhausen et al., "Decrease of vascular angiotensin sensitivity by L-dopa during human pregnancy," Am J Obstet Gynecol, 140(6):671-675 (1981).
Klemm et al., "Alterin angiotensin levels by administration of captopril or indomethacin or by angiotensin infusion, contributes to an understanding of atrial natriuretic peptide regulation in man," Clinical and Experimental Pharmacology and Physiology, 15(4):349-355 (1988).
Koch et al., "The influence of angiotensin infusion on the urine composition in individual kidney function tests," Can Med Assoc J, 104(10):905-907 (1971).
Matsuda et al., "Change of left artrial systolic pressure waveform in relation to left ventricular end-diastolic pressure," Circulation, 82(5):1659-1667 (1990).
McGibney et al., "Observations on the mechanism underlying the differences in exercise and isoprenaline tachycardia after cardioselective and non-selective beta-adrenoceptor antagonists," Br J Clin Pharmacol, 15(1):15-19 (1983).
Mehrotra et al., "Angiotensin infusion test in the diagnosis of renal hypertension," Journal of the Association of Physicians of India, 22(4):289-292 (1974).
Mendelsohn et al., "Renin, angiotensin II, and adrenal corticosteroid relationships during sodium deprivation and angiotensin infusion in normotensive and hypertensive man," Circ Res, 31(5):728-739 (1972).
Merillon et al., "Aortic input impedance in normal man and arterial hypertension: It's modification during changes in aortic pressure," Cardiovascular Research, 16(11):646-656 (1982).
Oelkers et al., "Arterial angiotensin II and venous immunoreactive material before and during angiotensin infusion in man," Clin Sci, 43(2):209-218 (1972).
Ogihara et al., "Clinical efficacy and tolerability of candesartan cilextil," J Hum Hypertens, 13(1):S27-S31 (1999).
Oney et al., "Effect of Angiotensin infusion during pregnancy on fetal heart rate and on fetal activity," Eur J Obstet Gynecol Reprod Biolm 13(3):133-137 (1982).
Parmley et al., "Dissociation between indices of pump performance and contractility in patients with coronary artery disease and acute myocardial infarction," Chest, 67(2):141-146 (1975).

Payne et al., "Comparison of isometric exercise and angiotensin infusion as stress test for evaluation of left ventricular function," Am J Cardiol, 31(4):428-433 (1973).
Rado et al., "Effects of ethacrynic acid on specific rental functions without and during angiotensin infusion in man," Arch Int Pharmacodyn, 186(1):142-154 (1970).
Rado et al., "Studies on the sites of action of ethacrynic acid and furosemide during angiotensin infusion," J Clin Pharmacol, 10(6):375-381 (1970).
Ronan et al., "The angiotensin infusion test as a method of evaluating left ventricular function," Am Heart J, 89(5):554-560 (1975).
Rouine-Rapp et al., "Effect of enalaprilat on postoperative hypertension after surgical repair of coarctation of the aorta," Pediatr Crit Care Med, 4(3):327-332 (2003).
Schachinger et al., "Angiotensin II decreases the renal MRI blood oxygenation level-dependent signal. Hypertension," American Heart Association, 47(6):1062-1066 (2006).
Schaison et al., "Angiotensin and adrenal steroidogenesis: Study of 21-hyroxylase-deficient congenital adrenal hyperplasia," J Clin Endocrinol Metab, 51(6):1390-1394 (1980).
Seidelin et al., "The effect of angiotensin II on haemodynamic and plasma noradrenaline responses to tyramine infusion in man," Eur J Clin Pharmacol, 41(2):119-123 (1991).
Semple et al., "Suppression of plasma ACTH concentration by angiotensin II infusion in normal humans and in a subject with a steroid 17 alpha-hydroxylase defect," Clin Endocrinol, 10(2):137-144 (1979).
Shen et al., "Evaluation of relationship between myocardial contractile state and left ventricular function in patients with aortic regurgitation," Circulation, 71(1):31-38 (1985).
Sluiter et al., "The nartriutetic effect of the dihydropyridine calcium antagonist felodipine: a placebo-controlled study involving intravenous angiotensin II in normotensive volunteers," Journal of Cardiovascular Pharmacology, 10(10):S154-S161 (1987).
Sowers et al., "Effects of dietary sodium on circadian rhythm and physiological responses of 18-hydroxycorticosterone," Clin Sci, 64(3):295-301 (1983).
Spark et al., "Activation of aldosterone secretion in primary aldosteronism," The Journal of Clinical Investigation, 48(1):96-104 (1969).
Speckart et al., "The effect of angiotensin II and indomethacin on immunoreactive prostaglandin "A" levels in man," Prostaglandins, 11(3):481-188 (1976).
Vingerhoedt et al., "Haemodynamic and pulse wave responses to intravenous infusions of angiotensin II during chronic telmisartan therapy in normal volunteers," J Renin Angiotensin Aldosterone Syst, 4(4):244-248 (2003).
Website: http://kidneyfund.org/kidney-disease/kidney-problems/acute-kidney-injury.html, retrieved on Feb. 4, 2019 (2019).
Widgren et al., "Low-dose angiotensin II increases glucose disposal rate during euglycemic hyperinsulinemia," Am J Hypertens, 6(10):892-895 (1993).
Woodland et al., "Hypertension corrected and aldosterone responsiveness to renin-angiotensin restored by long-term dexamethasone in glucocorticoid-suppressible hyperaldosteronism," Clin Exp Pharmacol Physiol, 12(3):245-248 (1985).

* cited by examiner

SEQUENCE LISTING

```
<160> NUMBER OF SEQ ID NOS: 18

<210> SEQ ID NO 1
<211> LENGTH: 8
<212> TYPE: PRT
<213> ORGANISM: Unknown
<220> FEATURE:
<223> OTHER INFORMATION: Description of Unknown:
      Angiotensin II peptide

<400> SEQUENCE: 1

Asp Arg Val Tyr Ile His Pro Phe
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Arg Val Tyr Val His Pro Phe
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Arg Val Phe Ile His Pro Phe
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Tyr Ile His Pro Phe
1               5
```

```
<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asn Arg Val Tyr Tyr Val His Pro Phe
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Arg Val Tyr Ile His Pro Ile
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Arg Val Tyr Ile His Pro Ala
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Diiodo-Tyr

<400> SEQUENCE: 8

Asn Arg Val Tyr Ile His Pro Phe
1               5

<210> SEQ ID NO 9
<211> LENGTH: 7
<212> TYPE: PRT
<213> ORGANISM: Unknown
<220> FEATURE:
<223> OTHER INFORMATION: Description of Unknown:
      Angiotensin III peptide

<400> SEQUENCE: 9

Arg Val Tyr Ile His Pro Phe
1               5

<210> SEQ ID NO 10
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 10

Arg Val Tyr Val His Pro Phe
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Val Phe Ile His Pro Phe
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Val Tyr Ile His Pro Ala
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Diiodo-Tyr

<400> SEQUENCE: 13

Arg Val Tyr Ile His Pro Phe
1               5

<210> SEQ ID NO 14
<211> LENGTH: 6
<212> TYPE: PRT
<213> ORGANISM: Unknown
<220> FEATURE:
<223> OTHER INFORMATION: Description of Unknown:
      Angiotensin IV peptide

<400> SEQUENCE: 14

Val Tyr Ile His Pro Phe
1               5

<210> SEQ ID NO 15
<211> LENGTH: 6
<212> TYPE: PRT
<213> ORGANISM: Artificial Sequence
<220> FEATURE:
```

```
-continued

<223> OTHER INFORMATION: Description of Artificial Sequence: Synthetic
      peptide

<400> SEQUENCE: 15

Val Tyr Val His Pro Phe
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Phe Ile His Pro Phe
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Tyr Ile His Pro Ala
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Diiodo-Tyr

<400> SEQUENCE: 18

Val Tyr Ile His Pro Phe
1               5
```

METHODS FOR ADMINISTERING ANGIOTENSIN II

RELATED APPLICATIONS

This application claims the benefit of priority to U.S. Provisional Patent Application Ser. No. 62/276,171, filed Jan. 7, 2016, and U.S. Provisional Patent Application Ser. No. 62/347,292, filed on Jun. 8, 2016, each of which are herein incorporated by reference in their entireties.

SEQUENCE LISTING

The instant application contains a Sequence Listing which has been submitted electronically in ASCII format and is hereby incorporated by reference in its entirety. Said ASCII copy, created on Feb. 27, 2017, is named LJH-02101_SL.txt and is 4,235 bytes in size.

BACKGROUND OF THE INVENTION

Hypotension, if uncorrected, is life-threatening and occurs as the result of various underlying conditions such as trauma, septic shock or drug reactions. The first line of treatment is intravenous fluids, and if this fails to correct the hypotension then vasopressors are deployed. The first line vasopressor is a catecholamine infusion. Catecholamines are amines derived from the amino acid tyrosine, and they include epinephrine (adrenaline), norepinephrine (noradrenaline), phenylephrine, and dopamine, which act as both hormones and neurotransmitters that increase blood pressure. While largely effective at treating hypotension, some patients fail to respond to adequate doses and are defined as catecholamine-resistant. These patients frequently have a high mortality and no acceptable alternatives.

The use of high doses of catecholamines in patients with severe hypotension is associated with poor outcomes. For example, the in-patient, 90-day mortality rate is 50-93% for patients who require norepinephrine as a vasopressor at doses that exceed 0.1 µg/kg/min, and 94% of patients who require norepinephrine at doses above 100 µg/min die.

Thus, alternate methods of regulating blood pressure in patients with catecholamine-resistant hypotension are needed.

SUMMARY OF THE INVENTION

Angiotensin II is a peptide hormone naturally produced by the body that regulates blood pressure via vasoconstriction and sodium reabsorption. The hemodynamic effects of angiotensin II administration have been the subject of numerous clinical studies, demonstrating significant effects on systemic and renal blood flow. The invention disclosed herein relates to methods of treating hypotension by administering angiotensin II, angiotensin III, or angiotensin IV to a patient.

Various aspects of the invention relate to the finding that some hypotensive patients display a more dramatic response to angiotensin II therapy than other hypotensive patients. Patients who display a dramatic response to angiotensin II may be deficient in angiotensin II, e.g., because one of the upstream mediators of angiotensin II is deficient. In contrast, hypotensive patients who are not deficient in angiotensin II may be relatively less sensitive to angiotensin II. Thus, the components of the pathway upstream of angiotensin II may be monitored prior to administering angiotensin II to a patient to determine an appropriate dose for the patient. For example, a high serum concentration of angiotensin I in a patient may indicate that the patient is not efficiently converting angiotensin I to angiotensin II, which may indicate that the patient will be acutely sensitive to subsequent angiotensin II therapy. Similarly, a patient with a low serum concentration of angiotensin II, or a high angiotensin I to angiotensin II ratio, may be acutely sensitive to angiotensin II therapy. Angiotensin I is converted to angiotensin II by angiotensin converting enzyme (ACE), which is located predominantly in the lung. Thus, patients with impaired lung function, such as patients with acute respiratory distress syndrome, may have lower endogenous angiotensin II production, and such patients may be particularly sensitive to angiotensin II therapy. Lower doses of angiotensin II therapy may be administered to hypotensive patients who are predicted to be sensitive to angiotensin II therapy relative to other hypotensive patients, e.g., to inhibit or prevent undesired side effects of exogenous angiotensin II, such as hypertension.

In some aspects, the invention relates to methods of treating hypotension, such as catecholamine-resistant hypotension, in a patient in need thereof, comprising administering to the patient a composition comprising angiotensin II, angiotensin III, or angiotensin IV. The term "catecholamine-resistant hypotension" as used herein refers to patients who require more than 15 µg/kg/min of dopamine, 0.1 µg/kg/min norepinephrine, or 0.1 µg/kg/min epinephrine as a vasopressor. Dopamine, norepinephrine, and epinephrine may be administered at rates higher than 15 µg/kg/min, 0.1 µg/kg/min, or 0.1 µg/kg/min, respectively, but elevated rates correlate with increased mortality.

In some embodiments, the invention relates to a method of treating hypotension in a human patient, comprising measuring a feature in the patient and administering a composition comprising angiotensin II, angiotensin III, or angiotensin IV to the patient. The feature may be, for example, a blood concentration of angiotensin II, a blood concentration of angiotensin I, or a ratio of the blood concentration of angiotensin I to the blood concentration of angiotensin II. The feature may be blood plasma renin activity, a blood concentration of angiotensin converting enzyme (ACE), a blood concentration of aldosterone, a blood concentration of anti-diuretic hormone (ADH), or a blood concentration of angiotensinogen. The feature may be lung function.

In some embodiments, the invention relates to a method of diagnosing acute respiratory distress syndrome (ARDS) in a human patient, comprising measuring a feature in the patient. The feature may be, for example, a blood concentration of angiotensin II, a blood concentration of angiotensin I, or a ratio of the blood concentration of angiotensin I to the blood concentration of angiotensin II. The feature may be a blood concentration of angiotensin converting enzyme (ACE) or a blood concentration of angiotensinogen.

In some embodiments, the invention relates to a method of diagnosing catecholamine-resistant hypotension (CRH) in a human patient, comprising measuring a feature in the patient. The feature may be, for example, a blood concentration of angiotensin II, a blood concentration of angiotensin I, or a ratio of the blood concentration of angiotensin I to the blood concentration of angiotensin II. The feature may be blood plasma renin activity, a blood concentration of angiotensin converting enzyme (ACE), a blood concentration of aldosterone, a blood concentration of anti-diuretic hormone (ADH), or a blood concentration of angiotensinogen. The feature may be lung function.

The method may comprise administering angiotensin II (or angiotensin III or angiotensin IV) at a first rate if a measurement is greater than a threshold value. The method may comprise administering angiotensin II (or angiotensin III or angiotensin IV) at a first rate if the measurement is greater than or equal to a threshold value (i.e., if the measurement is at least a threshold value). The method may comprise administering angiotensin II (or angiotensin III or angiotensin IV) at a second rate if the measurement is less than a threshold value. The method may comprise administering angiotensin II (or angiotensin III or angiotensin IV) at a second rate if the measurement is less than or equal to a threshold value. The first rate and/or second rate may be the initial rate at which angiotensin II (or angiotensin III or angiotensin IV) is administered to the patient.

The method may comprise administering angiotensin II (or angiotensin III or angiotensin IV) at a first rate if the measurement is less than a threshold value. The method may comprise administering angiotensin II (or angiotensin III or angiotensin IV) at a first rate if the measurement is less than or equal to a threshold value. The method may comprise administering angiotensin II (or angiotensin III or angiotensin IV) at a second rate if a measurement is greater than a threshold value. The method may comprise administering angiotensin II (or angiotensin III or angiotensin IV) at a second rate if the measurement is greater than or equal to a threshold value (i.e., if the measurement is at least a threshold value). The first rate and/or second rate may be the initial rate at which angiotensin II (or angiotensin III or angiotensin IV) is administered to the patient.

The measurement may be a measurement of a blood concentration of angiotensin II, a blood concentration of angiotensin I, or a ratio of the blood concentration of angiotensin I to the blood concentration of angiotensin II. The measurement may be a measurement of blood plasma renin activity, a blood concentration of angiotensin converting enzyme (ACE), a blood concentration of aldosterone, a blood concentration of anti-diuretic hormone (ADH), or a blood concentration of angiotensinogen. The measurement may be a measurement of lung function.

In some embodiments, the invention relates to a method of treating hypotension in a human patient, comprising determining whether the patient has acute respiratory distress syndrome and administering a composition comprising angiotensin II (or angiotensin III or angiotensin IV) to the patient. The method may comprise administering angiotensin II (or angiotensin III or angiotensin IV) at a first rate if the patient has acute respiratory distress syndrome. The method may comprise administering angiotensin II (or angiotensin III or angiotensin IV) at a second rate if the patient does not have acute respiratory distress syndrome. The first rate and/or second rate may be the initial rate at which angiotensin II (or angiotensin III or angiotensin IV) is administered to the patient.

In some embodiments, the invention relates to a method of treating hypotension in a human patient, comprising determining whether the patient received an angiotensin converting enzyme inhibitor (ACE inhibitor) within a preceding period of time and administering a composition comprising angiotensin II (or angiotensin III or angiotensin IV) to the patient. The method may comprise administering angiotensin II (or angiotensin III or angiotensin IV) at a first rate if the patient received an ACE inhibitor within the preceding period of time. The method may comprise administering angiotensin II (or angiotensin III or angiotensin IV) at a second rate if the patient did not receive an ACE inhibitor within the preceding period of time. The ACE inhibitor may be, for example, perindopril, captopril, enalapril, lisinopril, benazepril, fosinopril, moexipril, quinapril, trandolapril, or ramipril. The preceding period of time may be, for example, about 1 hour, about 2 hours, about 3, hours, about 4 hours, about 5 hours, about 6 hours, about 7 hours, about 8 hours, about 9 hours, about 10 hours, about 11 hours, about 12 hours, about 14 hours, about 16 hours, about 18 hours, about 20 hours, about 24 hours, about 30 hours, about 36 hours, about 48 hours, or about 72 hours. The preceding period of time may be about 1 day, about 2 days, about 3 days, about 4 days, about 5 days, about 6 days, or about 7 days. The preceding period of time may be about 1 hour to about 7 days, about 1 hour to about 72 hours, about 1 hour to about 48 hours, about 1 hour to about 24 hours, about 1 hour to about 12 hours, or about 1 day to about 7 days. The first rate and/or second rate may be the initial rate at which angiotensin II (or angiotensin III or angiotensin IV) is administered to the patient.

The first rate may be, for example, at least 1, 2, 3, 4, 5, 6, 7, 8, 9, 10, 11, 12, 13, 14, 15, 16, 17, 18, 19, 20, 25, 30, 35, 40, 45, or 50 ng/kg/min angiotensin II (or angiotensin III or angiotensin IV). The first rate may be greater than 1, 2, 3, 4, 5, 6, 7, 8, 9, 10, 11, 12, 13, 14, 15, 16, 17, 18, 19, 20, 25, 30, 35, 40, 45, or 50 ng/kg/min angiotensin II (or angiotensin III or angiotensin IV). The first rate may be less than 1, 2, 3, 4, 5, 6, 7, 8, 9, 10, 11, 12, 13, 14, 15, 16, 17, 18, 19, 20, 25, 30, 35, 40, 45, or 50 ng/kg/min angiotensin II (or angiotensin III or angiotensin IV). The first rate may be less than or equal to 1, 2, 3, 4, 5, 6, 7, 8, 9, 10, 11, 12, 13, 14, 15, 16, 17, 18, 19, 20, 25, 30, 35, 40, 45, or 50 ng/kg/min angiotensin II (or angiotensin III or angiotensin IV). The first rate may be about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, or about 50 ng/kg/min angiotensin II (or angiotensin III or angiotensin IV). The first rate may be about 0.1 ng/kg/min to 20 ng/kg/min, about 0.1 ng/kg/min to about 19 ng/kg/min, about 0.1 ng/kg/min to about 18 ng/kg/min, about 0.1 ng/kg/min to about 17.5 ng/kg/min, about 0.2 ng/kg/min to about 17.5 ng/kg/min, about 0.25 ng/kg/min to about 17.5 ng/kg/min, about 0.1 ng/kg/min to about 15 ng/kg/min, about 0.2 ng/kg/min to about 15 ng/kg/min, or about 0.25 ng/kg/min to about 15 ng/kg/min. The first rate may be about 0.5 ng/kg/min to 20 ng/kg/min, about 0.5 ng/kg/min to about 19 ng/kg/min, about 0.5 ng/kg/min to about 18 ng/kg/min, about 0.5 ng/kg/min to about 17.5 ng/kg/min, about 0.75 ng/kg/min to about 17.5 ng/kg/min, about 1.0 ng/kg/min to about 17.5 ng/kg/min, about 0.5 ng/kg/min to about 15 ng/kg/min, about 0.75 ng/kg/min to about 15 ng/kg/min, or about 1.0 ng/kg/min to about 15 ng/kg/min. The first rate may be 20 ng/kg/min to about 200 ng/kg/min, 20 ng/kg/min to about 120 ng/kg/min, 20 ng/kg/min to about 100 ng/kg/min, 20 ng/kg/min to about 90 ng/kg/min, 20 ng/kg/min to about 80 ng/kg/min, 20 ng/kg/min to about 70 ng/kg/min, 20 ng/kg/min to about 60 ng/kg/min, or 20 ng/kg/min to about 50 ng/kg/min.

The second rate may be, for example, at least 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 ng/kg/min angiotensin II (or angiotensin III or angiotensin IV). The second rate may be greater than 1, 2, 3, 4, 5, 6, 7, 8, 9, 10, 11, 12, 13, 14, 15, 16, 17, 18, 19, 20, 25, 30, 35, 40, 45, or 50 ng/kg/min angiotensin II (or angiotensin III or angiotensin IV). The second rate may be less than 20, 25, 30, 35, 40, 45, 50, 55, 60, 65, 70, 75, 80, 85, 90, 95, or 100 ng/kg/min angiotensin II (or angiotensin III or angiotensin IV). The second rate may be less than or equal to 20, 25, 30, 35, 40, 45, 50, 55, 60, 65, 70, 75, 80, 85, 90, 95, or 100 ng/kg/min angiotensin II (or angiotensin III or angiotensin IV). The second rate may be about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, about or 100 ng/kg/min angiotensin II (or angiotensin III or angiotensin IV). The second rate may be about 0.1 ng/kg/min to 20 ng/kg/min, about 0.1 ng/kg/min to about 19 ng/kg/min, about 0.1 ng/kg/min to about 18 ng/kg/min, about 0.1 ng/kg/min to about 17.5 ng/kg/min, about 0.2 ng/kg/min to about 17.5 ng/kg/min, about 0.25 ng/kg/min to about 17.5 ng/kg/min, about 0.1 ng/kg/min to about 15 ng/kg/min, about 0.2 ng/kg/min to about 15 ng/kg/min, or about 0.25 ng/kg/min to about 15 ng/kg/min. The second rate may be about 0.5 ng/kg/min to 20 ng/kg/min, about 0.5 ng/kg/min to about 19 ng/kg/min, about 0.5 ng/kg/min to about 18 ng/kg/min, about 0.5 ng/kg/min to about 17.5 ng/kg/min, about 0.75 ng/kg/min to about 17.5 ng/kg/min, about 1.0 ng/kg/min to about 17.5 ng/kg/min, about 0.5 ng/kg/min to about 15 ng/kg/min, about 0.75 ng/kg/min to about 15 ng/kg/min, or about 1.0 ng/kg/min to about 15 ng/kg/min. The second rate may be 20 ng/kg/min to about 200 ng/kg/min, 20 ng/kg/min to about 120 ng/kg/min, 20 ng/kg/min to about 100 ng/kg/min, 20 ng/kg/min to about 90 ng/kg/min, 20 ng/kg/min to about 80 ng/kg/min, 20 ng/kg/min to about 70 ng/kg/min, 20 ng/kg/min to about 60 ng/kg/min, or 20 ng/kg/min to about 50 ng/kg/min.

The feature may be a blood concentration of angiotensin II, and the threshold may be 10, 15, 20, 25, 30, 35, 40, 45, 50, 55, 60, 65, 70, 75, 80, 85, 90, 95, or 100 ng/mL. The method may comprise administering angiotensin II (or angiotensin III or angiotensin IV) at a first rate if the measured blood concentration of angiotensin II is less than (or less than or equal to) the threshold. The method may comprise administering angiotensin II (or angiotensin III or angiotensin IV) at a second rate if the measured blood concentration of angiotensin II is greater than (or greater than or equal to) the threshold. For example, the method may comprise administering angiotensin II at an initial rate of less than or equal to 20 ng/kg/min if the blood concentration of angiotensin II is less than or equal to 50 ng/mL. Similarly, the method may comprise administering angiotensin II at an initial rate of greater than or equal to 20 ng/kg/min if the blood concentration of angiotensin II is greater than 50 ng/mL. The method may comprise administering angiotensin II at an initial rate of less than 20 ng/kg/min if the blood concentration of angiotensin II is less than or equal to 50 ng/mL (or less than or equal to a different threshold). The method may comprise administering angiotensin II at an initial rate of greater than or equal to 20 ng/kg/min if the blood concentration of angiotensin II is greater than 50 ng/mL (or greater than a different threshold). The method may comprise diagnosing the patient with acute respiratory distress syndrome if the measured blood concentration of angiotensin II is less than (or less than or equal to) the threshold (e.g., less than 20 ng/kg/min). The method may comprise diagnosing the patient with catecholamine-resistant hypotension if the measured blood concentration of angiotensin II is less than (or less than or equal to) the threshold (e.g., less than 20 ng/kg/min).

The feature may be a blood concentration of angiotensin I, and the threshold may be 100, 150, 200, 250, 300, 350, 400, 450, 500, 550, 600, 650, 700, 750, 800, 850, 900, 950, or 1000 pg/mL. The method may comprise administering angiotensin II (or angiotensin III or angiotensin IV) at a first rate if the measured blood concentration of angiotensin I is greater than (or greater than or equal to) the threshold. The method may comprise administering angiotensin II (or angiotensin III or angiotensin IV) at a second rate if the measured blood concentration of angiotensin I is less than (or less than or equal to) the threshold. For example, the method may comprise administering angiotensin II at an initial rate of less than or equal to 20 ng/kg/min if the blood concentration of angiotensin I is at least 500 pg/mL. Similarly, the method may comprise administering angiotensin II at an initial rate of greater than or equal to 20 ng/kg/min if the blood concentration of angiotensin I is less than 500 pg/mL. The method may comprise administering angiotensin II at an initial rate of less than 20 ng/kg/min if the blood concentration of angiotensin I is at least 500 pg/mL (or at least a different threshold). Similarly, the method may comprise administering angiotensin II at an initial rate of greater than or equal to 20 ng/kg/min if the blood concentration of angiotensin I is less than 500 pg/mL (or less than a different threshold). The method may comprise diagnosing the patient with acute respiratory distress syndrome if the measured blood concentration of angiotensin I is greater than (or greater than or equal to) the threshold (e.g., greater than 500 pg/mL). The method may comprise diagnosing the patient with catecholamine-resistant hypotension if the measured blood concentration of angiotensin I is greater than (or greater than or equal to) the threshold (e.g., greater than 500 pg/mL).

The feature may be a ratio of the blood concentration of angiotensin I and the blood concentration of angiotensin II, and the threshold may be 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, or 20:1. The method may comprise administering angiotensin II (or angiotensin III or angiotensin IV) at a first rate if the measured ratio is greater than (or greater than or equal to) the threshold. The method may comprise administering angiotensin II (or angiotensin III or angiotensin IV) at a second rate if the measured ratio is less than (or less than or equal to) the threshold. For example, the method may comprise administering angiotensin II at an initial rate of less than or equal to 20 ng/kg/min if the ratio of angiotensin I to angiotensin II is at least 1:1. Similarly, the method may comprise administering angiotensin II at an initial rate of greater than or equal to 20 ng/kg/min if the ratio of angiotensin I to angiotensin II is less than 1:1. The method may comprise administering angiotensin II at an initial rate of less than 20 ng/kg/min if the ratio of angiotensin I to angiotensin II is at least 1:1 (or at least a different threshold). The method may comprise administering angiotensin II at an initial rate of greater than or equal to 20 ng/kg/min if the ratio of angiotensin I to angiotensin II is less than 1:1 (or less than a different threshold). The method may comprise diagnosing the patient with acute respiratory distress syndrome if the ratio of angiotensin I to angiotensin II is greater than (or greater than or equal to) the threshold (e.g., greater than 1:1). The method may comprise diagnosing the patient with catecholamine-resistant hypotension if the ratio of angiotensin I to angiotensin II is greater than (or greater than or equal to) the threshold (e.g., greater than 1:1).

The feature may be blood plasma renin activity, and the threshold may be 5.0, 4.0, 3.0, 2.0, 1.5, 1.2, 1.1, 1.0, 0.9, 0.8, 0.7, 0.6, 0.5, 0.4, 0.3, 0.2, or 0.1 µIU/mL. The method may comprise administering angiotensin II (or angiotensin III or angiotensin IV) at a first rate if the measured blood plasma renin activity is less than (or less than or equal to) the threshold. The method may comprise administering angiotensin II (or angiotensin III or angiotensin IV) at a second rate if the measured blood plasma renin activity is greater than (or greater than or equal to) the threshold. For example, the method may comprise administering angiotensin II at an initial rate of less than or equal to 20 ng/kg/min if the blood plasma renin activity is less than 1.2 µIU/mL. Similarly, the method may comprise administering angiotensin II at an initial rate of greater than or equal to 20 ng/kg/min if the blood concentration of blood plasma renin activity is at least 1.2 µIU/mL. The method may comprise administering angiotensin II at an initial rate of less than 20 ng/kg/min if the blood plasma renin activity is less than 1.2 µIU/mL (or less than a different threshold). The method may comprise administering angiotensin II at an initial rate of greater than or equal to 20 ng/kg/min if the blood concentration of blood plasma renin activity is at least 1.2 µIU/mL (or greater than or equal to a different threshold). The method may comprise diagnosing the patient with catecholamine-resistant hypotension if the blood plasma renin activity is less than (or less than or equal to) the threshold (e.g., less than 1.2 µIU/mL).

The feature may be a blood concentration of angiotensin converting enzyme (ACE), and the threshold may be 5, 10, 15, 20, 25, 30, 35, 40, 45, 50, 55, 60, 65, 70, 75, 80, 85, 90, 95, or 100 nmol/mL. The method may comprise administering angiotensin II (or angiotensin III or angiotensin IV) at a first rate if the measured blood concentration of ACE is less than (or less than or equal to) the threshold. The method may comprise administering angiotensin II (or angiotensin III or angiotensin IV) at a second rate if the measured blood concentration of ACE is greater than (or greater than or equal to) the threshold. For example, the method may comprise administering angiotensin II at an initial rate of less than or equal to 20 ng/kg/min if the blood concentration of ACE is less than 40 nmol/mL. Similarly, the method may comprise administering angiotensin II at an initial rate of greater than or equal to 20 ng/kg/min if the blood concentration of ACE is at least 40 nmol/mL. The method may comprise administering angiotensin II at an initial rate of less than 20 ng/kg/min if the blood concentration of ACE is less than 40 nmol/mL (or less than a different threshold). The method may comprise administering angiotensin II at an initial rate of greater than or equal to 20 ng/kg/min if the blood concentration of ACE is at least 40 nmol/mL (or greater than or equal to a different threshold). The method may comprise diagnosing the patient with acute respiratory distress syndrome if the blood concentration of ACE is less than (or less than or equal to) the threshold (e.g., less than 40 nmol/mL). The method may comprise diagnosing the patient with catecholamine-resistant hypotension if the blood concentration of ACE is less than (or less than or equal to) the threshold (e.g., less than 40 nmol/mL).

The feature may be a blood concentration of aldosterone, and the threshold may be 1, 2, 3, 4, 5, 6, 7, 8, 9, 10, 11, 12, 13, 14, 15, 16, 17, 18, 19, or 20 ng/dL. The method may comprise administering angiotensin II (or angiotensin III or angiotensin IV) at a first rate if the measured blood concentration of aldosterone is less than (or less than or equal to) the threshold. The method may comprise administering angiotensin II (or angiotensin III or angiotensin IV) at a second rate if the measured blood concentration of aldosterone is greater than (or greater than or equal to) the threshold. For example, the method may comprise administering angiotensin II at an initial rate of less than or equal to 20 ng/kg/min if the blood concentration of aldosterone is less than 5 ng/dL. Similarly, the method may comprise administering angiotensin II at an initial rate of greater than or equal to 20 ng/kg/min if the blood concentration of aldosterone is at least 5 ng/dL. The method may comprise administering angiotensin II at an initial rate of less than 20 ng/kg/min if the blood concentration of aldosterone is less than 5 ng/dL (or less than a different threshold). The method may comprise administering angiotensin II at an initial rate of greater than or equal to 20 ng/kg/min if the blood concentration of aldosterone is at least 5 ng/dL (or greater than or equal to a different threshold). The method may comprise diagnosing the patient with catecholamine-resistant hypotension if the blood concentration of aldosterone is less than (or less than or equal to) the threshold (e.g., less than 5 ng/dL).

The feature may be a blood concentration of anti-diuretic hormone (ADH), and the threshold may be 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, or 10.5 pg/mL. The method may comprise administering angiotensin II (or angiotensin III or angiotensin IV) at a first rate if the measured blood concentration of ADH is less than (or less than or equal to) the threshold. The method may comprise administering angiotensin II (or angiotensin III or angiotensin IV) at a second rate if the measured blood concentration of ADH is greater than (or greater than or equal to) the threshold. For example, the method may comprise administering angiotensin II at an initial rate of less than or equal to 20 ng/kg/min if the blood concentration of ADH is less than 2.5 pg/mL. Similarly, the method may comprise administering angiotensin II at an initial rate of greater than or equal to 20 ng/kg/min if the blood concentration of ADH is at least 2.5 pg/ml. The method may comprise administering angiotensin II at an initial rate of less than 20 ng/kg/min if the blood concentration of ADH is less than 2.5 pg/mL (or less than a different threshold). The method may comprise administering angiotensin II at an initial rate of greater than or equal to 20 ng/kg/min if the blood concentration of ADH is at least 2.5 pg/ml (or at least a different threshold). The method may comprise diagnosing the patient with catecholamine-resistant hypotension if the blood concentration of ADH is less than (or less than or equal to) the threshold (e.g., less than 2.5 pg/ml).

The feature may be a blood concentration of angiotensinogen, and the threshold may be 50, 100, 150, 200, 250, 300, 350, 400, 450, 500, 550, 600, 650, 700, 750, 800, 850, 900, or 950 ng/mL. The method may comprise administering angiotensin II (or angiotensin III or angiotensin IV) at a first rate if the measured blood concentration of angiotensinogen is greater than (or greater than or equal to) the threshold. The method may comprise administering angiotensin II (or angiotensin III or angiotensin IV) at a second rate if the measured blood concentration of angiotensinogen is less than (or less than or equal to) the threshold. For example, the method may comprise administering angiotensin II at an initial rate of less than or equal to 20 ng/kg/min if the blood concentration of angiotensinogen is at least 250 ng/mL. Similarly, the method may comprise administering angiotensin II at an initial rate of greater than or equal to 20 ng/kg/min if the blood concentration of angiotensinogen is less than or equal to 250 ng/mL. The method may comprise administering angiotensin II at an initial rate of less than 20 ng/kg/min if the blood concentration of angiotensinogen is at least 250 ng/mL (or greater than or equal to a different threshold). The method may comprise administering angiotensin II at an initial rate of greater than or equal to 20 ng/kg/min if the blood concentration of angiotensinogen is less than 250 ng/mL (or less than a different threshold). The method may comprise diagnosing the patient with acute respiratory distress syndrome if the blood concentration of angiotensinogen is greater than (or greater than or equal to) the threshold (e.g., greater than 250 ng/mL). The method may comprise diagnosing the patient with catecholamine-resistant hypotension if the blood concentration of angiotensinogen is greater than (or greater than or equal to) the threshold (e.g., greater than 250 ng/mL).

The feature may be lung function, and the method may comprise administering angiotensin II (or angiotensin III or angiotensin IV) to the patient at a first rate if the patient has impaired lung function. The feature may be lung function, and the method may comprise administering angiotensin II (or angiotensin III or angiotensin IV) to the patient at a second rate if the patient does not have impaired lung function. For example, the method may comprise administering angiotensin II at an initial rate of less than or equal to 20 ng/kg/min if the patient has impaired lung function. Similarly, the method may comprise administering angiotensin II at an initial rate of greater than or equal to 20 ng/kg/min if the patient does not have impaired lung function. The method may comprise administering angiotensin II at an initial rate of less than 20 ng/kg/min if the patient has impaired lung function.

Impaired lung function may be an acute or chronic lung condition selected from a respiratory disease, an inflammatory lung disease, a respiratory tract infection, a restrictive lung disease, lung cancer, a pleural cavity disease, a pulmonary vascular disease (such as a pulmonary embolism), acute respiratory distress syndrome, or lung trauma. "Measuring" lung function may include diagnosing the patient with an acute or chronic lung condition, or obtaining information related to lung function, such as by consulting a care provider of the patient, consulting a family member or an emergency contact of the patient, or by reviewing the medical history of the patient. For example, "measuring lung function" may comprise reviewing a medical record of a patient.

The method may comprise determining whether the patient has acute respiratory distress syndrome and administering a composition comprising angiotensin II (or angiotensin III or angiotensin IV) to the patient at a first rate if the patient has acute respiratory distress syndrome. The method may comprise determining whether the patient has acute respiratory distress syndrome and administering a composition comprising angiotensin II (or angiotensin III or angiotensin IV) to the patient at a second rate if the patient does not have acute respiratory distress syndrome. For example, the method may comprise administering angiotensin II at an initial rate of less than or equal to 20 ng/kg/min if the patient has acute respiratory distress syndrome. Similarly, the method may comprise administering angiotensin II at an initial rate of greater than or equal to 20 ng/kg/min if the patient does not have acute respiratory distress syndrome. The method may comprise administering angiotensin II at an initial rate of less than 20 ng/kg/min if the patient has acute respiratory distress syndrome.

The method may comprise determining whether the patient received an angiotensin converting enzyme inhibitor (ACE inhibitor) within a preceding period of time and administering a composition comprising angiotensin II (or angiotensin III or angiotensin IV) to the patient at a first rate if the patient received an ACE inhibitor within the preceding period of time. The method may comprise determining whether the patient received an angiotensin converting enzyme inhibitor (ACE inhibitor) within a preceding period of time and administering a composition comprising angiotensin II (or angiotensin III or angiotensin IV) to the patient at a second rate if the patient has not received an ACE inhibitor within the preceding period of time. For example, the method may comprise determining whether the patient received an ACE inhibitor within a preceding period of time (e.g., within 24 hours) and administering angiotensin II to the patient at an initial rate of less than or equal to 20 ng/kg/min if the patient received an ACE inhibitor within the preceding period of time. Similarly, the method may comprise determining whether the patient received an ACE inhibitor within a preceding period of time (e.g., within 24 hours) and administering angiotensin II to the patient at an initial rate of greater than or equal to 20 ng/kg/min if the patient did not receive an ACE inhibitor within the preceding period of time. The method may comprise determining whether the patient received an ACE inhibitor within a preceding period of time (e.g., within 24 hours) and administering angiotensin II to the patient at an initial rate of less than 20 ng/kg/min if the patient received an ACE inhibitor within the preceding period of time.

In some embodiments, the patient is receiving a vasopressor, i.e., other than the angiotensin II, angiotensin III, or angiotensin IV. The method may comprise decreasing the rate at which the vasopressor is administered.

The method may comprise measuring a mean arterial pressure (MAP) of the patient a subsequent period of time after administering to the patient the composition comprising angiotensin II (or angiotensin III or angiotensin IV). The term "mean arterial pressure" or "MAP" refers to the average arterial pressure during a single cardiac cycle. The method may comprise decreasing the rate at which a vasopressor is administered (i.e., a vasopressor other than the angiotensin II, angiotensin III, or angiotensin IV), if the measured mean arterial pressure is at or above 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 mm Hg (referred to as a target value or target MAP herein). For example, the method may comprise decreasing the rate at which a vasopressor is administered if the measured mean arterial pressure is at or above 75 mm Hg. The method may further comprise increasing the rate at which the angiotensin II (or angiotensin III or angiotensin IV) is administered if the measured mean arterial pressure is less than 75 mm Hg (or less than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 mm Hg, e.g., wherein the target MAP corresponds to the target MAP for decreasing the rate at which the vasopressor is administered).

A patient may have a known initial mean arterial pressure prior to administering the composition comprising angiotensin II, angiotensin III, or angiotensin IV (referred to as an initial mean arterial pressure herein, which is distinguished from a measured mean arterial pressure that is obtained after administering the composition to the patient). For example, the method may comprise measuring a mean arterial pressure prior to administering the composition to the patient. The method may comprise decreasing the rate at which a vasopressor is administered (i.e., a vasopressor other than the angiotensin II, angiotensin III, or angiotensin IV), if the measured mean arterial pressure (obtained a subsequent period of time after administering to the patient the composition) is at least 1, 2, 3, 4, 5, 6, 7, 8, 9, 10, 11, 12, 13, 14, 15, 16, 17, 18, 19, or 20 mm Hg higher than the initial mean arterial pressure. For example, the method may comprise decreasing the rate at which a vasopressor is administered if the measured mean arterial pressure is at least 10 mm Hg higher than the initial mean arterial pressure. The method may further comprise increasing the rate at which the angiotensin II (or angiotensin III or angiotensin IV) is administered if the measured mean arterial pressure is less than 10 mm Hg higher than the initial mean arterial pressure (or less than 1, 2, 3, 4, 5, 6, 7, 8, 9, 10, 11, 12, 13, 14, 15, 16, 17, 18, 19, or 20 mm Hg higher than the initial mean arterial pressure, e.g., wherein the threshold difference between the measured and initial MAP corresponds to the threshold difference for decreasing the rate at which the vasopressor is administered).

Those of skill in the art will recognize that in the context of the present invention, anti-hypotensive therapeutics can be administered in any suitable way, but are typically administered by continuous infusion. Accordingly, increasing or decreasing a rate of administration can be accomplished by changing the rate of flow of an intravenous drip, changing the concentration of the agent in an intravenous drip, etc. However, the manner in which the rate of administration is changed will depend on the mode of administration of the therapeutic. Where the therapeutic is administered transmucosally or transdermally, the rate may be increased by changing to a higher-release-rate patch or transdermal composition for example. Where the therapeutic is administered orally, the rate may be increased by switching to a higher-dose form, administering additional doses, or administering controlled-release dosage forms with a higher rate of release, for example. Where the therapeutic is administered by inhalation, the rate may be increased by administering additional boluses, a more concentrated bolus, or a faster-release bolus, for example. Other modes of administration (via subcutaneous injection pump, suppository, etc.) can be modulated in analogous fashions, and decreasing the rate of administration can be accomplished by doing the opposite of an action that would increase the rate of administration of the therapeutic.

Angiotensin II, angiotensin III, and angiotensin IV may be particularly useful for patients who require potentially harmful doses of vasopressors. Thus, in some embodiments, the invention relates to methods of treating hypotension, wherein, prior to administering the composition, the patient is receiving dopamine, dobutamine, norepinephrine, epinephrine, phenylephrine, terlipressin, vasopressin, a vasopressin analogue, or midodrine as a vasopressor. The vasopressor may be, for example, a catecholamine. The term "catecholamine", as used herein, refers to dopamine, norepinephrine, phenylephrine, and epinephrine and their prodrugs, structural analogs, or derivatives that induce similar physiological effects in humans, e.g., raise mean arterial pressure in healthy human subjects. In certain embodiments, the catecholamine may be dopamine, norepinephrine, or epinephrine. The vasopressor may be vasopressin or a vasopressin analogue. A vasopressin analogue may be, for example, terlipressin, argipressin, desmopressin, felypressin, lypressin, or ornipressin. In some embodiments, a method comprises administering two or more of angiotensin II, angiotensin III, angiotensin IV, a catecholamine, vasopressin, a vasopressin analog, dobutamine, and midodrine to a patient. For example, a method may comprise administering angiotensin II, a catecholamine, and either vasopressin or a vasopressin analog to a patient. A method may comprise administering angiotensin II, a catecholamine, and vasopressin to a patient.

In some embodiments, the invention relates to methods of treating hypotension wherein the patient has a cardiovascular sequential organ failure assessment score ("SOFA score") of 1 or greater prior to initiation of angiotensin II therapy (or angiotensin III therapy or angiotensin IV therapy). For example, a patient may have a cardiovascular SOFA score of 1, 2, 3, or 4. In some embodiments, the patient has a cardiovascular SOFA score of 2, 3, or 4. In other embodiments, the patient has a cardiovascular SOFA score of 3 or 4. In some embodiments, the patient has a cardiovascular SOFA score of 4 prior to initiation of angiotensin II therapy (or angiotensin III therapy or angiotensin IV therapy).

In some embodiments, the patient is receiving at least 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 µg/kg/min of norepinephrine prior to administration of angiotensin II (or angiotensin III or angiotensin IV). For example, prior to administering the composition, the patient may be receiving at least 0.1 µg/kg/min of norepinephrine. In some embodiments, the patient may be receiving at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 µg/min of norepinephrine prior to administering the composition.

Alternatively, hypotension may be treated with epinephrine. Thus, in some embodiments, the patient may be receiving at least 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 µg/kg/min of epinephrine prior to initiation of angiotensin II therapy (or angiotensin III therapy or angiotensin IV therapy). For example, prior to administering the composition, the patient may be receiving at least 0.1 µg/kg/min of epinephrine. In some embodiments, the patient may be receiving at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 µg/min of epinephrine prior to initiation of angiotensin II therapy (or angiotensin III therapy or angiotensin IV therapy).

Alternatively, hypotension may be treated with dopamine. Thus, in some embodiments, the patient may be receiving at least 5, 6, 7, 8, 9, 10, 11, 12, 13, 14, 15, 16, 17, 18, 19, 20, 21, 22, 23, 24, or 25 µg/kg/min of dopamine prior to initiation of angiotensin II therapy (or angiotensin III therapy or angiotensin IV therapy). For example, prior to administering the composition, the patient may be receiving at least 5 µg/kg/min of dopamine. In some embodiments, the patient may be receiving at least 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, or 2500 µg/min of dopamine prior to initiation of angiotensin II therapy (or angiotensin III therapy or angiotensin IV therapy).

Alternatively, hypotension may be treated with vasopressin. Thus, in some embodiments, the patient may be receiving at least 1, 2, 3, 4, 5, 6, 7, 8, 9, 10, 11, 12, 13, 14, 15, 16, 17, 18, 19, 20, 21, 22, 23, 24, or 25 mU/kg/min vasopressin. In some embodiments, the patient may be receiving at least 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.25, 0.30, 0.40, 0.50, 0.60, 0.70, 0.80, 0.90, 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5.0 U/min vasopressin. For example, prior to administering the composition, the patient may be receiving at least 0.01 U/min of vasopressin.

The patient's mean arterial pressure may be monitored to titrate angiotensin II, angiotensin III, angiotensin IV, or the vasopressor. For example, the patient's mean arterial pressure may be monitored with an indwelling arterial line or by other suitable methods. In some embodiments, an initial mean arterial pressure is measured prior to administering the composition, the composition is administered, and, after a subsequent period of time, an additional mean arterial pressure is measured. The subsequent period of time may be, for example, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 135, 150, 165, 180, 195, 210, 225, or 240 minutes, or about 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24, 25, 26, 27, 28, 29, 30, 31, 32, 33, 34, 35, 36, 37, 38, 39, 40, 41, 42, 43, 44, 45, 46, 47, or 48 hours or longer. Preferably, the subsequent period of time is less than two hours, most preferably about one hour or less.

In certain embodiments, if the measured mean arterial pressure meets or exceeds a target value, then the rate at which a vasopressor is administered is decreased. The target value may be, for example, 60, 61, 62, 63, 64, 65, 66, 67, 68, 69, 70, 71, 72, 73, 74, 75, 76, 77, 78, 79, or 80 mm Hg. In certain preferred embodiments, if the measured mean arterial pressure is at or above 75 mm Hg, then the rate at which a vasopressor is administered is decreased (i.e., any vasopressor, including angiotensin II, angiotensin III, angiotensin IV, a catecholamine, vasopressin, etc.).

In other embodiments, if the difference between the measured mean arterial pressure and the initial mean arterial pressure meets or exceeds a target value, then the rate at which a vasopressor is administered is decreased. The target value may be, for example, 1, 2, 3, 4, 5, 6, 7, 8, 9, 10, 11, 12, 13, 14, 15, 16, 17, 18, 19, 20, 21, 22, 23, 24, or 25 mm Hg. In certain preferred embodiments, if the measured mean arterial pressure is at least 10 mm Hg higher than the initial mean arterial pressure, then the rate at which a vasopressor is administered is decreased (i.e., any vasopressor, including angiotensin II, angiotensin III, angiotensin IV, a catecholamine, vasopressin, etc.).

The mean arterial pressure may be measured more than once; for example, the mean arterial pressure may be measured 1, 2, 3, 4, 5, 6, 7, 8, 9, 10, or more times, or even continuously or substantially continuously. The rate at which a vasopressor is administered may be decreased in response to each measurement (i.e., any vasopressor, including angiotensin II, angiotensin III, angiotensin IV, a catecholamine, vasopressin, etc.), depending on whether the measured mean arterial pressure meets or exceeds a target value. Similarly, the rate at which a vasopressor is administered may be increased after a measurement (i.e., any vasopressor, including angiotensin II, angiotensin III, angiotensin IV, a catecholamine, vasopressin, etc., if the measured mean arterial pressure is less than a target value. Similarly, the rate at which a vasopressor is administered may be decreased after each measurement (i.e., any vasopressor, including angiotensin II, angiotensin III, angiotensin IV, a catecholamine, vasopressin, etc.), depending on whether the difference between the measured mean arterial pressure and the initial mean arterial pressure is less than a target value. Similarly, the rate at which a vasopressor is administered may be increased after a measurement (i.e., any vasopressor, including angiotensin II, angiotensin III, angiotensin IV, a catecholamine, vasopressin, etc.), if the difference between the measured mean arterial pressure and the initial mean arterial pressure is less than a target value.

In some embodiments, if the patient's measured mean arterial pressure is at or above 75 mm Hg, then the rate at which a vasopressor is administered to the patient is decreased (i.e., any vasopressor, including angiotensin II, angiotensin III, and angiotensin IV). In some embodiments, if the patient's measured mean arterial pressure is at or above 65, 66, 67, 68, 69, 70, 71, 72, 73, 74, 75, 76, 77, 78, 79, 80, 81, 82, 83, 84, or 85 mm Hg, then the rate at which a vasopressor is administered to the patient is decreased (i.e., any vasopressor, including angiotensin II, angiotensin III, angiotensin IV, a catecholamine, vasopressin, etc.). In some embodiments, if the measured mean arterial pressure is at least 10 mm Hg higher than the initial mean arterial pressure, then the rate at which a vasopressor is administered to the patient is decreased (i.e., any vasopressor, including angiotensin II, angiotensin III, angiotensin IV, a catecholamine, vasopressin, etc.). In some embodiments, if the measured mean arterial pressure is at least 1, 2, 3, 4, 5, 6, 7, 8, 9, 10, 11, 12, 13, 14, 15, 16, 17, 18, 19, 20, 21, 22, 23, 24, or 25 mm Hg higher than the initial mean arterial pressure, then the rate at which a vasopressor is administered to the patient is decreased (i.e., any vasopressor, including angiotensin II, angiotensin III, angiotensin IV, a catecholamine, vasopressin, etc.). In certain embodiments, the rate at which a vasopressor is administered is decreased by at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or more (i.e., a vasopressor other than angiotensin II, angiotensin III, or angiotensin IV, e.g., which the patient is receiving prior to administering the composition). Thus, for example, the rate at which norepinephrine is administered may be decreased by at least 15%. In other embodiments, the rate at which a vasopressor (other than angiotensin II, angiotensin III, or angiotensin IV) is administered may be decreased by at least 60%. In some embodiments, the rate at which a vasopressor (other than angiotensin II, angiotensin III, or angiotensin IV) is administered is decreased to 0 µg/kg/min (or µg/min, 0 U/kg/min, or 0 U/min).

A vasopressor may be titrated down while monitoring a patient's MAP, and titration may occur over the course of minutes to hours. Thus, the rate at which a vasopressor is administered may be decreased by at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or more over the course of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 135, 150, 165, 180, 195, 210, 225, or 240 minutes, or over the course of about 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24, 25, 26, 27, 28, 29, 30, 31, 32, 33, 34, 35, 36, 37, 38, 39, 40, 41, 42, 43, 44, 45, 46, 47, or 48 hours or longer.

The rate of administration may be titrated by administering angiotensin II (or angiotensin III or angiotensin IV) at an initial rate and then increasing or decreasing the rate of administration. In some cases, the patient may be administered an initial bolus of angiotensin II (or angiotensin III or angiotensin IV) followed by the administration of angiotensin II (or angiotensin III or angiotensin IV) at a lower rate. Alternatively, the patient may be administered angiotensin II (or angiotensin III or angiotensin IV) at a low rate followed by gradual, elevated rates. Thus, in some embodiments, the method further comprises increasing the rate at which angiotensin II (or angiotensin III or angiotensin IV) is administered, and in other embodiments, the method further comprises decreasing the rate at which angiotensin II (or angiotensin III or angiotensin IV) is administered. For example, angiotensin II (or angiotensin III or angiotensin IV) may be administered at an initial rate of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20 ng/kg/min, and the rate may be increased to a final rate of about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 ng/kg/min. Alternatively, angiotensin II (or angiotensin III or angiotensin IV) may be administered at an initial rate of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 ng/kg/min, and the rate may be decreased to a final rate of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20 ng/kg/min. Angiotensin II (or angiotensin III or angiotensin IV) may be titrated while monitoring a patient's MAP, and titration may occur over the course of minutes to hours. Thus, the rate at which at which angiotensin II (or angiotensin III or angiotensin IV) is administered may be increased or decreased over the course of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 135, 150, 165, 180, 195, 210, 225, or 240 minutes, or over the course of about 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24, 25, 26, 27, 28, 29, 30, 31, 32, 33, 34, 35, 36, 37, 38, 39, 40, 41, 42, 43, 44, 45, 46, 47, or 48 hours or longer.

Angiotensin II (or angiotensin III or angiotensin IV) may be administered as long as necessary to maintain a MAP above a target value. Alternatively, angiotensin II (or angiotensin III or angiotensin IV) may be administered until the patient's MAP can be maintained at a lower dose of a vasopressor other than angiotensin II (or angiotensin III or angiotensin IV). In some embodiments, the composition is administered until the mean arterial pressure of the patient can be maintained at or above 70 mm Hg with less than 0.1 µg/kg/min norepinephrine, less than 0.1 µg/kg/min epinephrine, less than 15 µg/kg/min dopamine, or less than 0.01 U/min vasopressin. In other embodiments, the composition is administered continuously over a period of time selected from less than 6 hours; from 6 hours to 24 hours; or at least 24 hours. In other embodiments, the composition is administered continuously for at least 1-6 days, such as 1-11 days.

The methods disclosed herein can use any suitable form or analog of angiotensin II that exhibits the desired effect of increasing MAP in human subjects. In some embodiments, the angiotensin II has the sequence set forth in SEQ ID NO:1, 1 SEQ ID NO:2, SEQ ID NO:3, SEQ ID NO:4, SEQ ID NO:5, SEQ ID NO:6, SEQ ID NO:7, or SEQ ID NO:8. Preferably, the angiotensin II has the sequence set forth in SEQ ID NO:1.

In some embodiments, the angiotensin II is selected from 5-L-valine angiotensin II; 1-L-asparagine-5-L-valine angiotensin II; 1-L-asparagine-5-L-isoleucine angiotensin II; or 1-L-asparagine-5- L-isoleucine angiotensin II, preferably 5-L-isoleucine angiotensin II. The angiotensin II may be formulated as a pharmaceutically acceptable salt, for example, as an acetate salt.

The methods disclosed herein can use any suitable form or analog of angiotensin III that exhibits the desired effect of increasing MAP in human subjects. In some embodiments, the angiotensin III has the sequence set forth in SEQ ID NO:9, SEQ ID NO:10, SEQ ID NO:11, SEQ ID NO:12, or SEQ ID NO:13. Preferably, the angiotensin III has the sequence set forth in SEQ ID NO:9.

In some embodiments, the angiotensin III is selected from 4-L-valine angiotensin III or 4-L-isoleucine angiotensin III, preferably 4-L-isoleucine angiotensin III. The angiotensin III may be formulated as a pharmaceutically acceptable salt, for example, as an acetate salt.

The methods disclosed herein can use any suitable form or analog of angiotensin IV that exhibits the desired effect of increasing MAP in human subjects. In some embodiments, the angiotensin IV has the sequence set forth in SEQ ID NO:14, SEQ ID NO:15, SEQ ID NO:16, SEQ ID NO:17, or SEQ ID NO:18. Preferably, the angiotensin IV has the sequence set forth in SEQ ID NO:14.

In some embodiments, the angiotensin IV is selected from 3-L-valine angiotensin III or 3-L-isoleucine angiotensin IV, preferably 3-L-isoleucine angiotensin IV. The angiotensin IV may be formulated as a pharmaceutically acceptable salt, for example, as an acetate salt.

The composition may be formulated with varying concentrations of angiotensin II. Thus, in certain embodiments, the composition comprises angiotensin II at a concentration of about 1, 2, 3, 4, 5, 6, 7, 8, 9, 10, 15, 20, 25, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 550, 600, 650, 700, 750, 800, 850, 900, 950, 1000 µg/ml. In other embodiments, the composition comprises angiotensin II at a concentration of about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, or 25.0 mg/ml. Thus, in certain embodiments, the composition comprises angiotensin II at a concentration of about 2.5 mg/mL. The composition may comprise 0 mg/mL angiotensin II when the composition comprises angiotensin III and/or angiotensin IV.

The composition may be formulated with varying concentrations of angiotensin III. Thus, in certain embodiments, the composition comprises angiotensin III at a concentration of about 1, 2, 3, 4, 5, 6, 7, 8, 9, 10, 15, 20, 25, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 550, 600, 650, 700, 750, 800, 850, 900, 950, 1000 µg/ml. In other embodiments, the composition comprises angiotensin III at a concentration of about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, or 25.0 mg/ml. Thus, in certain embodiments, the composition comprises angiotensin III at a concentration of about 5 mg/mL. The composition may comprise 0 mg/mL angiotensin III when the composition comprises angiotensin II and/or angiotensin IV.

The composition may be formulated with varying concentrations of angiotensin IV. Thus, in certain embodiments, the composition comprises angiotensin IV at a concentration of about 1, 2, 3, 4, 5, 6, 7, 8, 9, 10, 15, 20, 25, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 550, 600, 650, 700, 750, 800, 850, 900, 950, 1000 µg/ml. In other embodiments, the composition comprises angiotensin IV at a concentration of about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, or 25.0 mg/ml. Thus, in certain embodiments, the composition comprises angiotensin IV at a concentration of about 5 mg/mL. The composition may comprise 0 mg/mL angiotensin IV when the composition comprises angiotensin II and/or angiotensin III.

In certain embodiments, the composition comprises an excipient, such as mannitol.

In certain embodiments, the composition is suitable for parenteral administration, such as injection or intravenous infusion, preferably intravenous infusion.

In some embodiments, the patient has sepsis. The patient may have septic shock, distributive shock, or cardiogenic shock.

In some embodiments, the patient is a mammal, such as a primate, ovine, porcine, canine, or rodent, preferably a human.

The rate of administration of the angiotensin II (or angiotensin III or angiotensin IV) can be modulated manually and/or automatically in response to measurements of the patient's mean arterial pressure obtained periodically or sporadically during treatment, e.g., to maintain a mean arterial pressure at this level, or within a predetermined range (e.g., 80-110 mm Hg).

In certain embodiments, the invention provides a method of assessing the response of a patient (such as a human) with hypotension to angiotensin II, angiotensin III, or angiotensin IV therapy, comprising administering to the patient an initial dose of a composition comprising angiotensin II, angiotensin III, or angiotensin IV (which may be a therapeutic dose or a sub-therapeutic dose, for example, a dose less than 1 ng/kg/min or about 1 ng/kg/min) and testing the patient for a change in a therapeutic parameter (e.g., blood pressure). For example, the therapeutic parameter of the patient can be assessed prior to administering the initial dose and again after administering the initial dose (e.g., at least half an hour later, preferably at least one hour later and/or up to 8 hours later, preferably up to 6 hours later, such as between 1 and 6 hours after administering the initial dose). Comparing the assessment of the therapeutic parameter after administering the initial dose to the assessment made prior to administering the initial dose will indicate whether the parameter is increasing or decreasing as a result of the angiotensin II, angiotensin III, or angiotensin IV therapy. Typically, an increase in the patient's blood pressure is indicative of a positive response to the angiotensin II, angiotensin III, and/or angiotensin IV therapy. In certain embodiments, where the patient exhibits a positive response to the therapy, the method further comprises administering an additional dose of angiotensin II, angiotensin III, or angiotensin IV to the patient. If a patient exhibits a negative response (e.g., a decrease in the patient's blood pressure), the patient will typically receive no additional doses of angiotensin II, angiotensin III, or angiotensin IV. If a patient exhibits no response or an insignificant response, the method may further comprise administering a higher dose of the composition than the initial dose and further testing the patient for a response to the higher dose. Alternatively, if the patient exhibits no response or an insignificant response, the patient may receive no further doses of angiotensin II, angiotensin III, or angiotensin IV therapy.

Angiotensin Therapeutics

Angiotensin II, angiotensin III, and angiotensin IV are peptide hormones naturally produced by the body that regulates blood pressure via vasoconstriction and sodium reabsorption. Hemodynamic effects of angiotensin II administration have been the patient of numerous clinical studies, demonstrating significant effects on systemic and renal blood flow (Harrison-Bernard, L. M., *The renal renin-angiotensin system*. Adv Physiol Educ, 33(4):270 (2009)). Angiotensin II is a hormone produced by the renin angiotensin aldosterone system (RAAS) that modulates blood pressure via regulation of vascular smooth muscle tone and extracellular fluid homeostasis. Angiotensin II mediates its effects on the vasculature by inducing vasoconstriction and sodium retention, and so is the target of many therapies for hypertension. In addition to its systemic effects, angiotensin II has a pronounced effect on the efferent arterioles of the kidney, maintaining glomerular filtration when blood flow is decreased. Angiotensin II also regulates sodium reabsorption in the kidney by stimulating Na+/H+exchangers in the proximal tubule and inducing the release of aldosterone and vasopressin (Harrison-Bernard, L. M., *The renal renin-angiotensin system*. Adv Physiol Educ, 33(4):270 (2009)).

The angiotensin II therapeutic that may be used for in the compositions and methods of this disclosure may be Asp-Arg-Val-Tyr-Ile-His-Pro-Phe (SEQ ID NO: 1) also called 5-isoleucine angiotensin II. SEQ ID NO: 1 is an octa-peptide naturally present in humans and other species, such as equines, hogs, etc. Isoleucine may be substituted by valine to result in 5-valine angiotensin II, Asp-Arg-Val-Tyr-Val-His-Pro-Phe (SEQ ID NO: 2). Other angiotensin II analogues such as [Asn$^1$-Phe$^4$]-angiotensin II (SEQ ID NO: 3), hexapeptide Val-Tyr-Ile-His-Pro-Phe (SEQ ID NO: 4), nonapeptide Asn-Arg-Val-Tyr-Tyr-Val-His-Pro-Phe (SEQ ID NO: 5), [Asn$^1$-Ile$^5$-Ile$^8$]-angiotensin II (SEQ ID NO: 6), [Asn$^1$-Ile$^5$-Ala$^8$]-angiotensin II (SEQ ID NO: 7), and [Asn$^1$-diiodoTyr$^4$-Ile$^5$]-angiotensin II (SEQ ID NO: 8) may also be used. Angiotensin II may be synthesized, for example, by solid phase peptide synthesis to incorporate modifications, such as C-terminal amidation. The term "angiotensin II", without further specificity, is intended to refer to any of these various forms, as well as combinations thereof.

In some aspects, a composition comprising angiotensin II may be selected from 5-valine angiotensin II, 5-valine angiotensin II amide, 5-L-isoleucine angiotensin II, and 5-L-isoleucine angiotensin II amide, or a pharmaceutically acceptable salt thereof, preferably manufactured under current good manufacturing conditions (cGMP). In some aspects, the composition may include different forms of angiotensin II in different percentages, e.g., a mixture of hexapeptide and nonapeptide angiotensin. The composition comprising angiotensin II may be suitable for parenteral administration, e.g., for injection or intravenous infusion.

The sequence of angiotensin II used in the compositions and methods disclosed herein may be homologous to the sequences of angiotensin II described above. In certain aspects, the invention includes isolated, synthetic, or recombinant amino acid sequences that are at least 80%, 85%, 90%, 95%, 97%, 98%, 99% or 100% identical to SEQ ID NO: 1, 2, 3, 4, 5, 6, 7, and/or 8. Any such variant sequences may be used in place of an angiotensin II as described in the preceding paragraph.

Angiotensin III is a metabolite of angiotensin II with approximately 40% of the activity of angiotensin II. An angiotensin III therapeutic that may be used for in the compositions and methods of this disclosure may be Arg-Val-Tyr-Ile-His-Pro-Phe (SEQ ID NO: 9). SEQ ID NO: 9 is an hepta-peptide naturally present in humans and other species, such as equines, hogs, etc. Isoleucine may be substituted by valine to result in Arg-Val-Tyr-Val-His-Pro-Phe (SEQ ID NO: 10). Other angiotensin III analogues such as [Phe$^3$]-angiotensin III (SEQ ID NO: 11), [Ile$^3$-Ala$^7$]-angiotensin III (SEQ ID NO: 12), and [diiodoTyr$^3$-Ile$^4$]-angiotensin III (SEQ ID NO: 13) may also be used. Angiotensin III may be synthesized, for example, by solid phase peptide synthesis to incorporate modifications, such as C-terminal amidation. The term "angiotensin III", without further specificity, is intended to refer to any of these various forms, as well as combinations thereof.

In some aspects, a composition comprising angiotensin III may be selected from 4-valine angiotensin III, 4-valine angiotensin III amide, 4-L-isoleucine angiotensin III, and 4-L-isoleucine angiotensin III amide, or a pharmaceutically acceptable salt thereof, preferably manufactured under current good manufacturing conditions (cGMP). A composition comprising angiotensin III may be suitable for parenteral administration, e.g., for injection or intravenous infusion.

Angiotensin IV is a metabolite of angiotensin III with less activity than angiotensin II. An angiotensin IV therapeutic that may be used for in the compositions and methods of this disclosure may be Val-Tyr-Ile-His-Pro-Phe (SEQ ID NO: 14). SEQ ID NO: 14 is an hexa-peptide naturally present in humans and other species, such as equines, hogs, etc. Isoleucine may be substituted by valine to result in Val-Tyr-Val-His-Pro-Phe (SEQ ID NO: 15). Other angiotensin IV analogues such as [Phe$^2$]-angiotensin IV (SEQ ID NO: 16), [Ile$^3$-Ala$^6$]-angiotensin IV (SEQ ID NO: 17), and [diiodoTyr$^2$-Ile$^3$]-angiotensin IV (SEQ ID NO: 18) may also be used. Angiotensin IV may be synthesized, for example, by solid phase peptide synthesis to incorporate modifications, such as C-terminal amidation. The term "angiotensin IV", without further specificity, is intended to refer to any of these various forms, as well as combinations thereof.

In some aspects, a composition comprising angiotensin IV may be selected from 3-valine angiotensin IV, 3-valine angiotensin IV amide, 3-L-isoleucine angiotensin IV, and 3-L-isoleucine angiotensin IV amide, or a pharmaceutically acceptable salt thereof, preferably manufactured under current good manufacturing conditions (cGMP). A composition comprising angiotensin IV may be suitable for parenteral administration, e.g., for injection or intravenous infusion.

An angiotensin II, angiotensin III, or angiotensin IV therapeutic may be used as any suitable salt, deprotected form, acetylated form, deacetylated form, and/or prodrug form of the above-mentioned peptides, including pegylated forms of the peptides or conjugates as disclosed in US Patent Publication 2011/0081371 (incorporated by reference). The term "prodrug" refers to any precursor compound which is able to generate or to release the above-mentioned peptide under physiological conditions. Such prodrugs may be larger peptides which are selectively cleaved in order to form the peptide of the invention. For example, in some aspects, the prodrug may be angiotensinogen, angiotensin I, or its homologues that may result in angiotensin II by the action of certain endogenous or exogenous enzymes. Further prodrugs include peptides with protected amino acids, e.g., having protecting groups at one or more carboxylic acid and/or amino groups. Suitable protecting groups for amino groups include the benzyloxycarbonyl, t-butyloxycarbonyl (BOC), fluorenylmethyloxycarbonyl (FMOC), formyl, and acetyl or acyl group. Suitable protecting groups for the carboxylic acid group include esters such as benzyl esters or t-butyl esters. The present invention also contemplates the use of angiotensin II, angiotensin III, angiotensin IV and/or precursor peptides having amino acid substitutions, deletions, additions, the substitutions and additions including the standard D and L amino acids and modified amino acids, such as, for example, amidated and acetylated amino acids, wherein the therapeutic activity of the base peptide sequence is maintained at a pharmacologically useful level.

Doses of the Therapeutically Effective Substance

In general, angiotensin II, angiotensin III, and angiotensin IV increase blood pressure, and patients who are hypotensive may require larger doses to exhibit pressor responses similar to those observed in normal patients. The composition including the angiotensin therapeutic (e.g., angiotensin II, angiotensin III, or angiotensin IV) can be administered at a rate sufficient to achieve an increase in blood pressure of at least about 10-15 mm Hg and optionally for at least angiotensin therapeutic administered may be varied in response to changes in other physiological parameters such as renal vascular resistance, renal blood flow, filtration fractions, mean arterial pressure, etc. For example, the rate of administration of the angiotensin therapeutic may start from about 2 ng/kg/min to about 20 ng/kg/min and is increased based on the mean arterial pressure ("MAP"). In some aspects, the rate of administration may be increased such that the MAP does not exceed about 70 mm Hg, about 80 mm Hg, about 90 mm Hg, about 100 mm Hg, about 110 mm Hg, etc. For example, a patient may be coupled to a monitor that provides continuous, periodic, or occasional measurements of MAP during some or all of the course of treatment. The rate of administration may be modulated manually (e.g., by a physician or nurse) or automatically (e.g., by a medical device capable of modulating delivery of the composition in response to MAP values received from the monitor) to maintain the patient's MAP within a desired range (e.g., 80-110 mm Hg) or below a desired threshold, e.g., as set forth above.

The composition including the angiotensin therapeutic may be administered over a period of time selected from at least 8 hours; at least 24 hours; and from 8 hours to 24 hours. The composition including the angiotensin therapeutic may be administered continuously for at least 2-6 days, such as 2-11 days, continuously for 2-6 days, for 8 hours a day over a period of at least 2-6 days, such as 2-11 days. A weaning period (from several hours to several days) may be beneficial after prolonged infusion.

The composition including the angiotensin therapeutic may further include one or more additional pharmaceutical agent. For example, angiotensin II, angiotensin III, or angiotensin IV may be administered with albumin. The quantity of the additional pharmaceutical agent administered may vary depending on the cumulative therapeutic effect of the treatment including the angiotensin therapeutic and the additional pharmaceutical agent. For example, the quantity of albumin administered may be 1 gram of albumin per kilogram of body weight given intravenously on the first day, followed by 20 to 40 grams daily. Yet other additional pharmaceutical agents may be any one or more of midodrine, octreotide, somatostatin, vasopressin analogue ornipressin, terlipressin, pentoxifylline, acetylcysteine, norepinephrine, misoprostol, etc. In some aspects, other natriuretic peptides may also be used in combination with the angiotensin therapeutic to remedy the impairment of sodium excretion associated with diseases discussed above. For example, natriuretic peptides may include any type of atrial natriuretic peptide (ANP), brain natriuretic peptide (BNP), C-type natriuretic peptide (CNP), and/or dendroaspis natriuretic peptide, etc. Several diuretic compounds may be used in combination with the angiotensin therapeutic to induce urine output. For example any one or more of the xanthines such as caffeine, theophylline, theobromine; thiazides such as bendroflumethiazide, hydrochlorothiazide; potassium-sparing diuretics such as amiloride, spironolactone, triamterene, potassium canrenoate; osmotic diuretics such as glucose (especially in uncontrolled diabetes), mannitol; loop diuretics such as bumetanide, ethacrynic acid, furosemide, torsemide; carbonic anhydrase inhibitors such as acetazolamide, dorzolamide; Na-H exchanger antagonists such as dopamine; aquaretics such as goldenrod, juniper; arginine vasopressin receptor 2 antagonists such as amphotericin B, lithium citrate; acidifying salts such as $CaCl_2$, $NH_4Cl$; ethanol, water, etc. may be used in combination with the angiotensin therapeutic to treat the patient. The list of additional pharmaceutical agents described above is merely illustrative and may include any other pharmaceutical agents that may be useful for the treatment of hypotension and related conditions.

Excipients

The pharmaceutical compositions of the present invention may also contain diluents, fillers, salts, buffers, stabilizers, solubilizers, and other materials well known in the art. The term "pharmaceutically acceptable carrier" refers to a non-toxic carrier that may be administered to a patient, together with a therapeutically effective substance (such as angiotensin II) of this invention, and which does not destroy the pharmacological activity of the therapeutically effective substance. The term "pharmaceutically acceptable" means a non-toxic material that does not interfere with the effectiveness of the biological activity of the active ingredient(s). The characteristics of the carrier will depend on the route of administration. The term "excipient" refers to an additive in a formulation or composition that is not a pharmaceutically active ingredient.

One of skill in the art would appreciate that the choice of any one excipient may influence the choice of any other excipient. For example, the choice of a particular excipient may preclude the use of one or more additional excipients because the combination of excipients would produce undesirable effects. One of skill in the art would be able to empirically determine which excipients, if any, to include in the compositions of the invention. Excipients of the invention may include, but are not limited to, co-solvents, solubilizing agents, buffers, pH adjusting agents, bulking agents, surfactants, encapsulating agents, tonicity-adjusting agents, stabilizing agents, protectants, and viscosity modifiers. In some aspects, it may be beneficial to include a pharmaceutically acceptable carrier in the compositions of the invention.

Solubilizing Agents

In some aspects, it may be beneficial to include a solubilizing agent in the compositions of the invention. Solubilizing agents may be useful for increasing the solubility of any of the components of the formulation or composition, including a therapeutically effective substance (e.g., angiotensin II, angiotensin III, or angiotensin IV) or an excipient. The solubilizing agents described herein are not intended to constitute an exhaustive list, but are provided merely as exemplary solubilizing agents that may be used in the compositions of the invention. In certain aspects, solubilizing agents include, but are not limited to, ethyl alcohol, tert-butyl alcohol, polyethylene glycol, glycerol, methylparaben, propylparaben, polyethylene glycol, polyvinyl pyrrolidone, and any pharmaceutically acceptable salts and/or combinations thereof.

pH-adjusting Agents

In some aspects, it may be beneficial to adjust the pH of the compositions by including a pH-adjusting agent in the compositions of the invention. Modifying the pH of a formulation or composition may have beneficial effects on, for example, the stability or solubility of a therapeutically effective substance, or may be useful in making a formulation or composition suitable for parenteral administration. pH-adjusting agents are well known in the art. Accordingly, the pH-adjusting agents described herein are not intended to constitute an exhaustive list, but are provided merely as exemplary pH-adjusting agents that may be used in the compositions of the invention. pH-adjusting agents may include, for example, acids and bases. In some aspects, a pH-adjusting agent includes, but is not limited to, acetic acid, hydrochloric acid, phosphoric acid, sodium hydroxide, sodium carbonate, and combinations thereof.

The pH of the compositions of the invention may be any pH that provides desirable properties for the formulation or composition. Desirable properties may include, for example, therapeutically effective substance (e.g., angiotensin II, angiotensin III, or angiotensin IV) stability, increased therapeutically effective substance retention as compared to compositions at other pHs, and improved filtration efficiency. In some aspects, the pH of the compositions of the invention may be from about 3.0 to about 9.0, e.g., from about 5.0 to about 7.0. In particular aspects, the pH of the compositions of the invention may be $5.5\pm0.1$, $5.6\pm0.1$, $5.7\pm0.1$, $5.8\pm0.1$, $5.9\pm0.1$, $6.0\pm0.1$, $6.1\pm0.1$, $6.2\pm0.1$, $6.3\pm0.1$, $6.4\pm0.1$, or $6.5\pm0.1$.

Buffers

In some aspects, it may be beneficial to buffer the pH by including one or more buffers in the compositions. In certain aspects, a buffer may have a pKa of, for example, about 5.5, about 6.0, or about 6.5. One of skill in the art would appreciate that an appropriate buffer may be chosen for inclusion in compositions of the invention based on its pKa and other properties. Buffers are well known in the art. Accordingly, the buffers described herein are not intended to constitute an exhaustive list, but are provided merely as exemplary buffers that may be used in the compositions of the invention. In certain aspects, a buffer may include one or more of the following: Tris, Tris HCl, potassium phosphate, sodium phosphate, sodium citrate, sodium ascorbate, combinations of sodium and potassium phosphate, Tris/Tris HCl, sodium bicarbonate, arginine phosphate, arginine hydrochloride, histidine hydrochloride, cacodylate, succinate, 2-(N-morpholino)ethanesulfonic acid (MES), maleate, bistris, phosphate, carbonate, and any pharmaceutically acceptable salts and/or combinations thereof.

Surfactants

In some aspects, it may be beneficial to include a surfactant in the compositions of the invention. Surfactants, in general, decrease the surface tension of a liquid composition. This may provide beneficial properties such as improved ease of filtration. Surfactants also may act as emulsifying agents and/or solubilizing agents. Surfactants are well known in the art. Accordingly, the surfactants described herein are not intended to constitute an exhaustive list, but are provided merely as exemplary surfactants that may be used in the compositions of the invention. Surfactants that may be included include, but are not limited to, sorbitan esters such as polysorbates (e.g., polysorbate 20 and polysorbate 80), lipopolysaccharides, polyethylene glycols (e.g., PEG 400 and PEG 3000), poloxamers (i.e., pluronics), ethylene oxides and polyethylene oxides (e.g., Triton X-100), saponins, phospholipids (e.g., lecithin), and combinations thereof.

Tonicity-adjusting Agents

In some aspects, it may be beneficial to include a tonicity-adjusting agent in the compositions of the invention. The tonicity of a liquid composition is an important consideration when administering the composition to a patient, for example, by parenteral administration. Tonicity-adjusting agents, thus, may be used to help make a formulation or composition suitable for administration. Tonicity-adjusting agents are well known in the art. Accordingly, the tonicity-adjusting agents described herein are not intended to constitute an exhaustive list, but are provided merely as exemplary tonicity-adjusting agents that may be used in the compositions of the invention. Tonicity-adjusting agents may be ionic or non-ionic and include, but are not limited to, inorganic salts, amino acids, carbohydrates, sugars, sugar alcohols, and carbohydrates. Exemplary inorganic salts may include sodium chloride, potassium chloride, sodium sulfate, and potassium sulfate. An exemplary amino acid is glycine. Exemplary sugars may include sugar alcohols such as glycerol, propylene glycol, glucose, sucrose, lactose, and mannitol.

Stabilizing Agents

In some aspects, it may be beneficial to include a stabilizing agent in the compositions of the invention. Stabilizing agents help increase the stability of a therapeutically effective substance in compositions of the invention. This may occur by, for example, reducing degradation or preventing aggregation of a therapeutically effective substance. Without wishing to be bound by theory, mechanisms for enhancing stability may include sequestration of the therapeutically effective substance from a solvent or inhibiting free radical oxidation of the anthracycline compound. Stabilizing agents are well known in the art. Accordingly, the stabilizing agents described herein are not intended to constitute an exhaustive list, but are provided merely as exemplary stabilizing agents that may be used in the compositions of the invention. Stabilizing agents may include, but are not limited to, emulsifiers and surfactants.

Routes of Delivery

The compositions of the invention can be administered in a variety of conventional ways. In some aspects, the compositions of the invention are suitable for parenteral administration. These compositions may be administered, for example, intraperitoneally, intravenously, intrarenally, or intrathecally. In some aspects, the compositions of the invention are injected intravenously. One of skill in the art would appreciate that a method of administering a therapeutically effective substance formulation or composition of the invention would depend on factors such as the age, weight, and physical condition of the patient being treated, and the disease or condition being treated. The skilled worker would, thus, be able to select a method of administration optimal for a patient on a case-by-case basis.

Unless otherwise defined herein, scientific and technical terms used in this application shall have the meanings that are commonly understood by those of ordinary skill in the art. Generally, nomenclature and techniques relating to chemistry, molecular biology, cell and cancer biology, immunology, microbiology, pharmacology, and protein and nucleic acid chemistry, described herein, are those well-known and commonly used in the art.

Throughout this specification, the word "comprise" or variations such as "comprises" or "comprising" will be understood to imply the inclusion of a stated integer (or components) or group of integers (or components), but not the exclusion of any other integer (or components) or group of integers (or components). The singular forms "a," "an," and "the" include the plurals unless the context clearly dictates otherwise. The term "including" is used to mean "including but not limited to." "Including" and "including but not limited to" are used interchangeably. The terms "patient" and "individual" are used interchangeably and refer to either a human or a non-human animal. These terms include mammals such as humans, primates, livestock animals (e.g., bovines, porcines), companion animals (e.g., canines, felines) and rodents (e.g., mice, rabbits and rats).

"About" and "approximately" shall generally mean an acceptable degree of error for the quantity measured given the nature or precision of the measurements. Typically, exemplary degrees of error are within 20%, preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Incorporation by Reference

All publications and patents mentioned herein are hereby incorporated by reference in their entirety as if each individual publication or patent was specifically and individually indicated to be incorporated by reference. In case of conflict, the present specification, including its specific definitions, will control. While specific aspects of the patient matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

What is claimed is:

1. A method of treating hypotension in a human patient, comprising:
   measuring a ratio of blood concentration of angiotensin I to blood concentration of angiotensin II in the patient; and
   administering to the patient a composition comprising angiotensin II.

2. The method of claim 1, wherein the method comprises administering angiotensin II at an initial rate of less than 10 ng/kg/min if the ratio of angiotensin I to angiotensin II is at least 1:1.

3. The method of claim 1, comprising administering angiotensin II at an initial rate of greater than or equal to 10 ng/kg/min if the ratio of angiotensin I to angiotensin II is less than 1:1.

4. The method of claim 1, wherein the patient has acute respiratory distress syndrome.

5. The method of claim 1, wherein the patient has an initial mean arterial pressure of 75 mm Hg or less prior to administering the composition.

6. The method of claim 1, further comprising:
   measuring a mean atrial blood pressure of the patient; and
   increasing the rate of administering angiotensin II if the mean arterial blood pressure is less than 75 mm Hg.

7. The method of claim 1, wherein the composition comprises 5-L-valine angiotensin II; 1-L-asparagine-5-L-valine angiotensin II; 1-L-asparagine-5-L-isoleucine angiotensin II; or 5-L-isoleucine angiotensin II.

8. The method of claim 1, wherein administering the composition comprises administering the composition by injection or intravenous infusion.

9. The method of claim 1, wherein the patient has a cardiovascular sequential organ failure assessment score ("SOFA score") of 3 or 4 prior to administering the composition.

10. The method of claim 1, wherein the patient has sepsis, septic shock, distributive shock, or cardiogenic shock.

11. The method of claim 1, wherein the method comprises administering angiotensin II at an initial rate of less than 5 ng/kg/min if the ratio of angiotensin I to angiotensin II is at least 1:1.

12. The method of claim 1, comprising administering angiotensin II at an initial rate of greater than or equal to 5 ng/kg/min if the ratio of angiotensin I to angiotensin II is less than 1:1.

13. A method of treating hypotension in a human patient receiving a vasopressor and having an initial mean arterial pressure, comprising:
measuring a ratio of angiotensin I to angiotensin II;
administering to the patient a composition comprising angiotensin II in the patient;
after a subsequent period of time, measuring the mean arterial pressure of the patient; and
if the measured mean arterial pressure is at or above 75 mm Hg, decreasing the rate at which the vasopressor is administered to the patient.

14. The method of claim 13, wherein the method comprises administering angiotensin II at an initial rate of less than 20 ng/kg/min if the ratio of angiotensin I to angiotensin II is at least 1:1.

15. The method of claim 13, comprising administering angiotensin II at an initial rate of greater than or equal to 20 ng/kg/min if the ratio of angiotensin I to angiotensin II is less than 1:1.

16. A method of treating hypotension in a human patient receiving a vasopressor and having an initial mean arterial pressure, comprising:
measuring a ratio of blood concentration of angiotensin I to blood concentration of angiotensin II in the patient;
administering to the patient a composition comprising angiotensin II;
after a subsequent period of time, measuring the mean arterial pressure of the patient; and
if the measured mean arterial pressure is at least 10 mm Hg higher than the initial mean arterial pressure, decreasing the rate at which the vasopressor is administered to the patient.

* * * * *